(12) United States Patent
Tsusaka et al.

(10) Patent No.: US 10,603,131 B2
(45) Date of Patent: Mar. 31, 2020

(54) INSTRUMENT FOR ARTIFICIAL KNEE JOINT REPLACEMENT SURGERY, AND INSTRUMENT UNIT FOR ARTIFICIAL KNEE JOINT REPLACEMENT SURGERY

(71) Applicant: KYOCERA Medical Corporation, Osaka-shi, Osaka (JP)

(72) Inventors: Shinya Tsusaka, Osaka (JP); Masahiko Hashida, Osaka (JP)

(73) Assignee: KYOCERA CORPORATION, Kyoto (JP)

( * ) Notice: Subject to any disclaimer, the term of this patent is extended or adjusted under 35 U.S.C. 154(b) by 476 days.

(21) Appl. No.: 15/327,222

(22) PCT Filed: Sep. 9, 2015

(86) PCT No.: PCT/JP2015/075579
§ 371 (c)(1),
(2) Date: Jan. 18, 2017

(87) PCT Pub. No.: WO2016/052110
PCT Pub. Date: Apr. 7, 2016

(65) Prior Publication Data
US 2017/0151031 A1    Jun. 1, 2017

(30) Foreign Application Priority Data

Sep. 30, 2014   (JP) ................................. 2014-202024

(51) Int. Cl.
*A61B 17/56*   (2006.01)
*A61B 90/00*   (2016.01)
(Continued)

(52) U.S. Cl.
CPC .............. *A61B 90/06* (2016.02); *A61B 17/56* (2013.01); *A61F 2/4657* (2013.01); *A61F 2/38* (2013.01); *A61F 2002/4668* (2013.01)

(58) Field of Classification Search
CPC .............. A61B 90/06; A61B 2090/067; A61B 2090/068; A61B 2002/4668; A61F 2/4657; A61F 2002/4659
(Continued)

(56) References Cited

U.S. PATENT DOCUMENTS 5,141,512 A * 8/1992 Farmer .............. A61B 17/1746
606/87
5,464,406 A   11/1995 Ritter et al.
(Continued)

FOREIGN PATENT DOCUMENTS

EP    2611379 A    7/2013
GB    2398011 A    8/2004
(Continued)

OTHER PUBLICATIONS

International Search Report, PCT/JP2015/075579, dated Dec. 8, 2015, 2 pgs.

*Primary Examiner* — Matthew J Lawson
(74) *Attorney, Agent, or Firm* — Volpe and Koenig, P.C.

(57) ABSTRACT

The instrument for artificial knee joint replacement surgery includes a holding mechanism that includes a holding portion having a contact portion to be brought into contact with a contact target of a patient on whom artificial knee joint replacement surgery is to be performed and that holds the patient in a state in which the contact portion is in contact with the contact target, and an indicating mechanism that is attached to the holding mechanism and includes a position identification target indicating portion to be arranged at a position corresponding to a position identification target in a state in which the holding mechanism holds the patient. The position at which the position identification target indicating portion is to be arranged is determined based on a positional relationship between the contact target and the
(Continued)

position identification target that is obtained in advance prior to surgery.

10 Claims, 14 Drawing Sheets

(51) Int. Cl.
*A61F 2/46* (2006.01)
*A61F 2/38* (2006.01)
(58) Field of Classification Search
USPC ........................................................ 606/102
See application file for complete search history.

(56) References Cited

U.S. PATENT DOCUMENTS

| | | | |
|---|---|---|---|
| 8,588,892 B2* | 11/2013 | Hladio | A61F 2/4609 |
| | | | 600/409 |
| 8,672,862 B2 | 3/2014 | Kanekasu | |
| 2005/0027303 A1* | 2/2005 | Lionberger | A61B 90/10 |
| | | | 606/102 |
| 2005/0203540 A1* | 9/2005 | Broyles | A61B 17/1742 |
| | | | 606/102 |
| 2007/0024448 A1 | 2/2007 | Sayegh | |
| 2009/0076507 A1* | 3/2009 | Claypool | A61B 90/06 |
| | | | 606/53 |
| 2009/0125029 A1 | 5/2009 | Seo et al. | |
| 2009/0216247 A1* | 8/2009 | Collette | A61B 17/155 |
| | | | 606/130 |
| 2012/0029581 A1* | 2/2012 | Kanekasu | A61B 90/06 |
| | | | 606/86 R |
| 2012/0130376 A1* | 5/2012 | Loring | A61B 17/025 |
| | | | 606/80 |
| 2013/0041288 A1* | 2/2013 | Taylor | A61B 5/6878 |
| | | | 600/587 |
| 2015/0157468 A1 | 6/2015 | Wakayama et al. | |
| 2016/0213382 A1* | 7/2016 | Maeda | A61B 17/155 |
| 2016/0367382 A1* | 12/2016 | Zai Ma; Hironori | A61B 5/1121 |

FOREIGN PATENT DOCUMENTS

| | | |
|---|---|---|
| JP | 2008-125706 | 6/2008 |
| JP | 4652481 B1 | 3/2011 |
| JP | 2012-029769 A | 2/2012 |
| WO | 2012/027816 A1 | 3/2012 |
| WO | 2014/025051 A1 | 2/2014 |

* cited by examiner

INSTRUMENT FOR ARTIFICIAL KNEE JOINT REPLACEMENT SURGERY, AND INSTRUMENT UNIT FOR ARTIFICIAL KNEE JOINT REPLACEMENT SURGERY

CROSS-REFERENCE TO RELATED APPLICATION

This application is based upon and claims the benefit of priority from Japanese patent application No. 2014-202024, the disclosure of which is herein incorporated by reference in its entirety.

BACKGROUND OF THE INVENTION

1. Field of the Invention

The present invention relates to an instrument to be used in artificial knee joint replacement surgery, and particularly to an instrument for finding a position of a predetermined portion in a patient.

2. Description of Related Art

When an artificial knee joint is attached to the knee joint of a patient, it is preferable to attach the artificial knee joint to the patient by using, as an index, an alignment in which the femoral head center, the knee joint center, and the second metatarsal bone of the patient are aligned in a straight line. However, since the femoral head center is located inside a human body, it is relatively difficult to confirm the position of the femoral head center, and thus surgery is sometimes performed in a state in which the position of the femoral head center is not accurately understood.

In this respect, Japanese Patent No. 4652481 discloses a femoral head center position identifying apparatus capable of identifying the position of the femoral head center, for example. This apparatus includes a marking plate that is to be arranged so as to cover a portion in which the femoral head center is located in a direction orthogonal to a frontal plane, a rotation arm having a rotation shaft that is to be arranged so as to extend in the direction orthogonal to the frontal plane, and a marker that is attached to the rotation arm and draws an arc on the marking plate with the rotation of the rotation arm. In this apparatus, the rotation arm is rotated at positions in a state in which a hip joint is positioned at a first position and a second position by being adducted and abducted, and thus the marker draws two arcs on the marking plate. The femoral head center can be identified as an intersection point of the two arcs drawn in such a manner.

SUMMARY OF THE INVENTION

However, when the above-described apparatus is used to identify the femoral head center, relatively complex operations such as fixing the marking plate to an operating table and fixing the rotating arm to the distal end of the femur of a patient are required during surgery.

The present invention was achieved to solve the aforementioned problems, and it is an object thereof to provide an instrument for artificial knee joint replacement surgery with which the position of a desired portion in a patient's body can be easily identified, and an instrument unit for artificial knee joint replacement surgery.

(1) An instrument for artificial knee joint replacement surgery according to one aspect of the present invention for achieving the above-mentioned object includes a holding mechanism that includes a holding portion having a contact portion to be brought into contact with a contact target of a patient on whom artificial knee joint replacement surgery is to be performed and that holds the patient in a state in which the contact portion is in contact with the contact target, and an indicating mechanism that includes a position identification target indicating portion to be arranged at a position corresponding to a position identification target in a state in which the holding mechanism holds the patient, the position identification target being a portion whose position is to be identified in the patient, and that is attached to the holding mechanism, wherein a position at which the position identification target indicating portion is to be arranged is determined based on a positional relationship between the contact target and the position identification target that is obtained in advance prior to surgery.

With this configuration, the position identification target indicating portion is arranged at a position corresponding to the position identification target in a state in which the contact portion is in contact with the contact target in the patient. At this time, the position identification target indicating portion is arranged based on a previously obtained relative positional relationship between the contact target and the position identification target in the patient. Accordingly, the position identification target indicating portion can be accurately arranged at the position corresponding to the position identification target. An operator who is to perform artificial knee joint replacement surgery can directly and visually observe the position identification target indicating portion arranged as described above and thus easily find the position of the position identification target in the patient.

Therefore, with this configuration, the position of a desired portion (position identification target) in the patient's body can be easily identified.

(2) It is preferable that a recessed portion into which the contact target is to be fitted is formed in the contact portion.

With this configuration, the contact portion can hold the patient in close contact.

(3) It is more preferable that the holding portion further includes a contact portion attachment portion with the contact portion being attachable to and detachable from, and the contact target is to be fitted into the recessed portion of the contact portion attached to the contact portion attachment portion.

With this configuration, the contact portion in which the recessed portion corresponding to the shape of the contact target in the patient is formed can be brought into contact with the contact target in the patient. Accordingly, the contact portion can hold the patient in closer contact.

(4) It is preferable that the recessed portion is formed based on a shape of the contact target in the patient.

With this configuration, the recessed portion of the contact portion is formed based on the shape of the contact target in the patient. Accordingly, the contact portion is customized based on the shape of the contact target in the patient, and therefore, the contact portion can hold the patient in even closer contact.

(5) It is preferable that the holding mechanism further includes a pair of the holding portions, and a connecting portion that connects the pair of the holding portions, and the holding mechanism holds the patient by the contact portions of the pair of the holding portions holding a pair of the contact targets therebetween.

With this configuration, the contact target in the patient is held between the pair of contact portions, and thus the instrument for artificial knee joint replacement surgery can be easily fixed to the patient.

(6) It is preferable that a hole portion into which an end portion of an alignment rod is to be inserted is formed in the position identification target indicating portion.

With this configuration, the alignment rod for confirming alignment (alignment in which the femoral head center, the knee joint center, and the second metatarsal bone center are aligned in a straight line) that is important during artificial knee joint replacement surgery can be appropriately arranged on the human body. Specifically, an operator can confirm the alignment in a state in which the alignment rod is attached to a hole portion of the position identification target indicating portion, that is, one end portion of the alignment rod is fixed at a position corresponding to the position of the femoral head. Accordingly, the appropriate alignment in which the position of the femoral head is accurately reflected can be confirmed.

(7) It is preferable that the contact target is one of left and right anterior superior iliac spines of the patient, and the position identification target is a femoral head of the patient.

With this configuration, the position identification target indicating portion is arranged at a position corresponding to the position of the femoral head based on the positional relationship between the anterior superior iliac spine and the femoral head that was obtained in advance prior to the surgery in a state in which the contact portion is in contact with the anterior superior iliac spine. Here, the above-described anterior superior iliac spine is a portion of the pelvis that protrudes laterally and is covered with only a very thin layer (e.g., skin). That is, the relative positional relationship between the contact portion brought into contact with the anterior superior iliac spine via this thin layer and the position identification target indicating portion is substantially the same as the previously obtained relative positional relationship between the anterior superior iliac spine and the femoral head. Accordingly, a large positional difference between the position of the position identification target indicating portion and the actual position of the femoral head can be prevented. Therefore, with this configuration, the position of the femoral head can be found accurately.

(8) It is more preferable that the indicating mechanism includes a base end portion that is a portion located on a base end side, and a front end portion that is a portion located on a front end side, the base end portion is attached to the holding mechanism, and the front end portion is formed to extend in a direction away from the base end portion, and the position identification target indicating portion is provided at a front end of the front end portion.

With this configuration, the position identification target indicating portion can be arranged at a position corresponding to the position of the femoral head that is positionally separated from the anterior superior iliac spine (contact target).

(9) It is more preferable that the front end portion can be moved relative to the base end portion in a direction in which the front end portion extends.

With this configuration, the position of the front end portion can be easily adjusted by moving the front end portion relative to the base end portion. Accordingly, the position of the position identification target indicating portion can be adjusted appropriately.

(10) It is preferable that the holding mechanism further includes a universal joint portion, and the base end portion is attached to the universal joint portion.

With this configuration, the base end portion can be rotated relative to the holding mechanism, and thus the orientation of the indicating mechanism can be easily adjusted. Accordingly, the position of the position identification target indicating portion can be adjusted appropriately.

(11) It is preferable that the contact target is a lateral malleolus at a distal end of a fibula or a medial malleolus at a distal end of a tibia of the patient, and the position identification target is a second metatarsal bone of the patient.

With this configuration, the position identification target indicating portion is arranged at a position corresponding to the position of the second metatarsal bone based on the positional relationship between the lateral malleolus at the distal end of the fibula (or the medial malleolus at the distal end of the tibia) and the second metatarsal bone that was obtained in advance prior to the surgery in a state in which the contact portion is in contact with the lateral malleolus or the medial malleolus. Here, the above-described lateral malleolus and medial malleolus are portions (so-called malleoli) at the distal end of the lower limb that protrude laterally and are covered with only a very thin layer (e.g., skin). That is, the position of the contact portion brought into contact with the lateral malleolus (or medial malleolus) via this thin layer relative to the position identification target indicating portion is substantially the same as the previously obtained position of the lateral malleolus (or medial malleolus) relative to the second metatarsal bone. Accordingly, a large positional difference between the position of the position identification target indicating portion and the actual position of the second metatarsal bone can be prevented. Therefore, with this configuration, the position of the second metatarsal bone as the position identification target can be found accurately.

(12) It is more preferable that the holding mechanism further includes a pair of the contact portions, and a connecting portion that connects the pair of the contact portions, and one of the contact portions is brought into contact with the lateral malleolus at the distal end of the fibula, the other contact portion is brought into contact with the medial malleolus at the distal end of the tibia, and the contact portions can be moved along the connecting portion.

With this configuration, the lateral malleolus at the distal end of the fibula and the medial malleolus at the distal end of the tibia are held between the pair of contact portions, and thus the instrument for artificial knee joint replacement surgery can be easily fixed to the patient.

(13) It is more preferable that the position identification target indicating portion is provided in the connecting portion, and an indicator for measuring a distance between a reference position of the connecting portion that corresponds to a position at which the position identification target indicating portion is provided and the contact portion is formed in the connecting portion.

With this configuration, the position of the contact portion relative to the reference position (position at which the position identification target indicating portion is provided) of the connecting portion is adjusted based on the positional relationship between the lateral malleolus at the distal end of the fibula (or the medial malleolus at the distal end of the tibia) and the second metatarsal bone of the patient that was obtained in advance through modeling of the bones of the patient, or the like. Specifically, an operator can match the distance between the reference position and the contact portion with the distance between the second metatarsal bone and the lateral malleolus (or medial malleolus) of the patient obtained through modeling or the like while checking the indicator. Accordingly, the position identification target indicating portion can be accurately arranged at the position of the second metatarsal bone.

(14) An instrument unit for artificial knee joint replacement surgery according to one aspect of the present invention for achieving the above-mentioned object includes a femoral head position determining instrument serving as the instrument for artificial knee joint replacement surgery that uses the femoral head of the patient as the position identification target, and a second metatarsal bone position determining instrument serving as the instrument for artificial knee joint replacement surgery that uses the second metatarsal bone of the patient as the position identification target.

With this configuration, the alignment can be confirmed using the alignment rod during and after the surgery in a state in which both the femoral head position determining instrument and second metatarsal bone position determining instrument are fixed to the patient. Specifically, in the state in which both of the instruments are fixed to the patient, an operator arranges the alignment rod such that both of the end portions of the alignment rod respectively overlap the position identification target indicating portion of the femoral head position determining instrument and the position identification target indicating portion of the second metatarsal bone position determining instrument. At this time, when the knee joint center overlaps the alignment rod, it can be confirmed that the femoral head center, the knee joint center, and the second metatarsal bone center are aligned in a straight line, that is, are in alignment. On the other hand, when there is a positional difference between the alignment rod and the knee joint center, it can be confirmed that they are not aligned, thus making it possible to determine whether or not osteotomy needs to be performed again based on the amount of the positional difference.

DETAILED DESCRIPTION OF THE INVENTION

Figure 1:
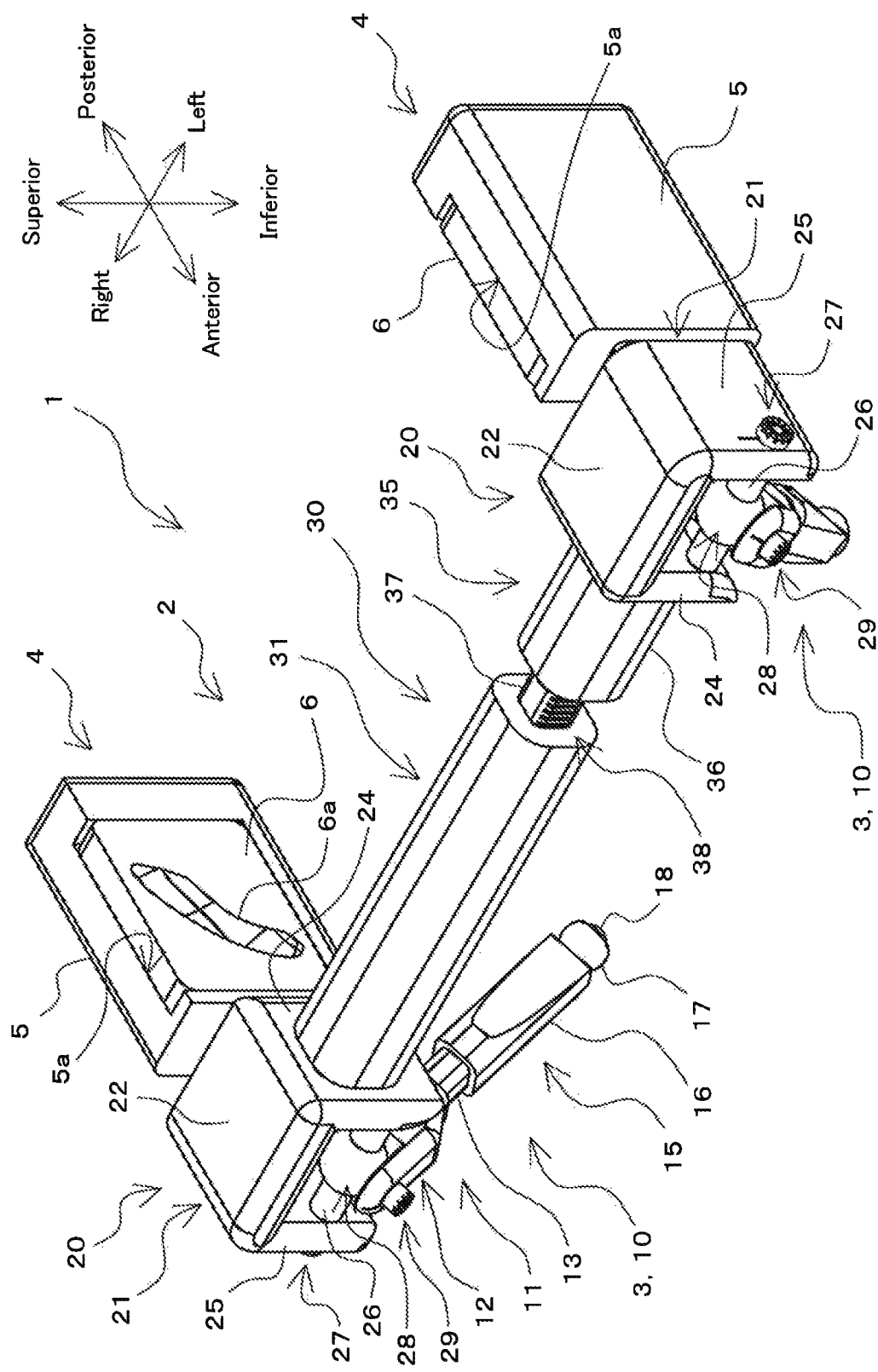
FIG. 1 is a perspective view of a femoral head position determining instrument according to an embodiment.
Figure 2:
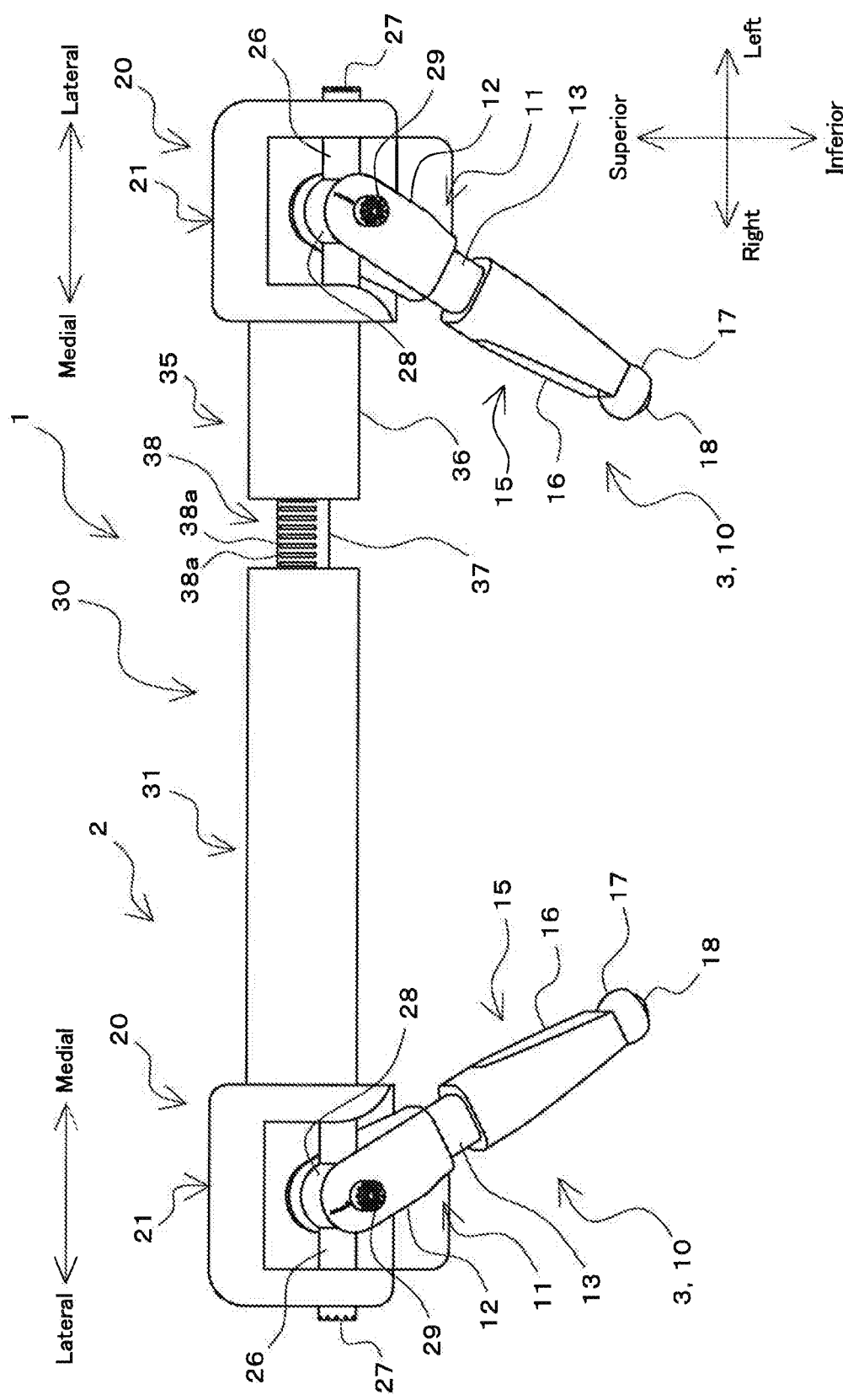
FIG. 2 is a front view of the femoral head position determining instrument shown in FIG. 1.
Figure 3:
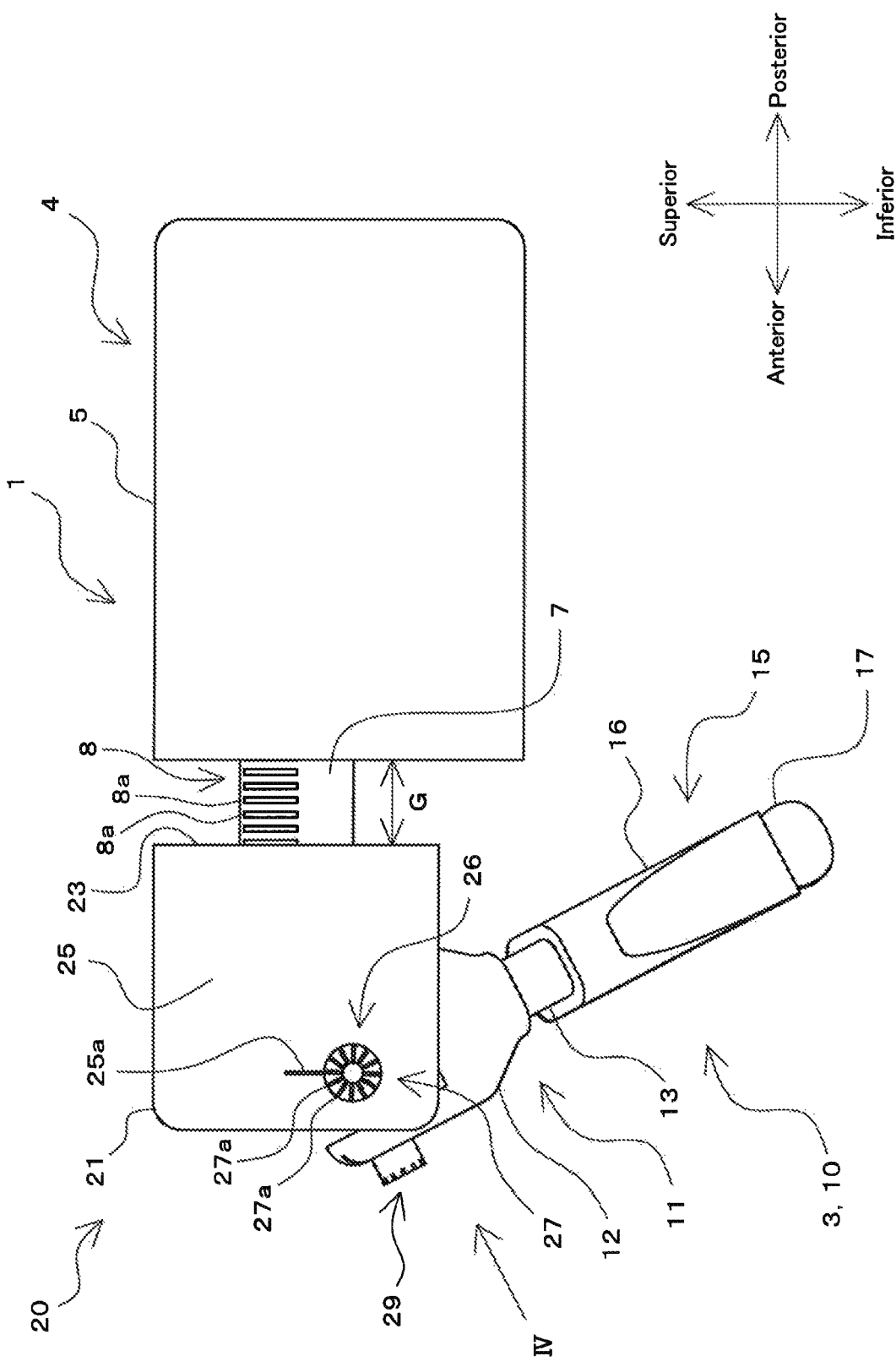
FIG. 3 is a side view of the femoral head position determining instrument shown in FIG. 1.
Figure 4:
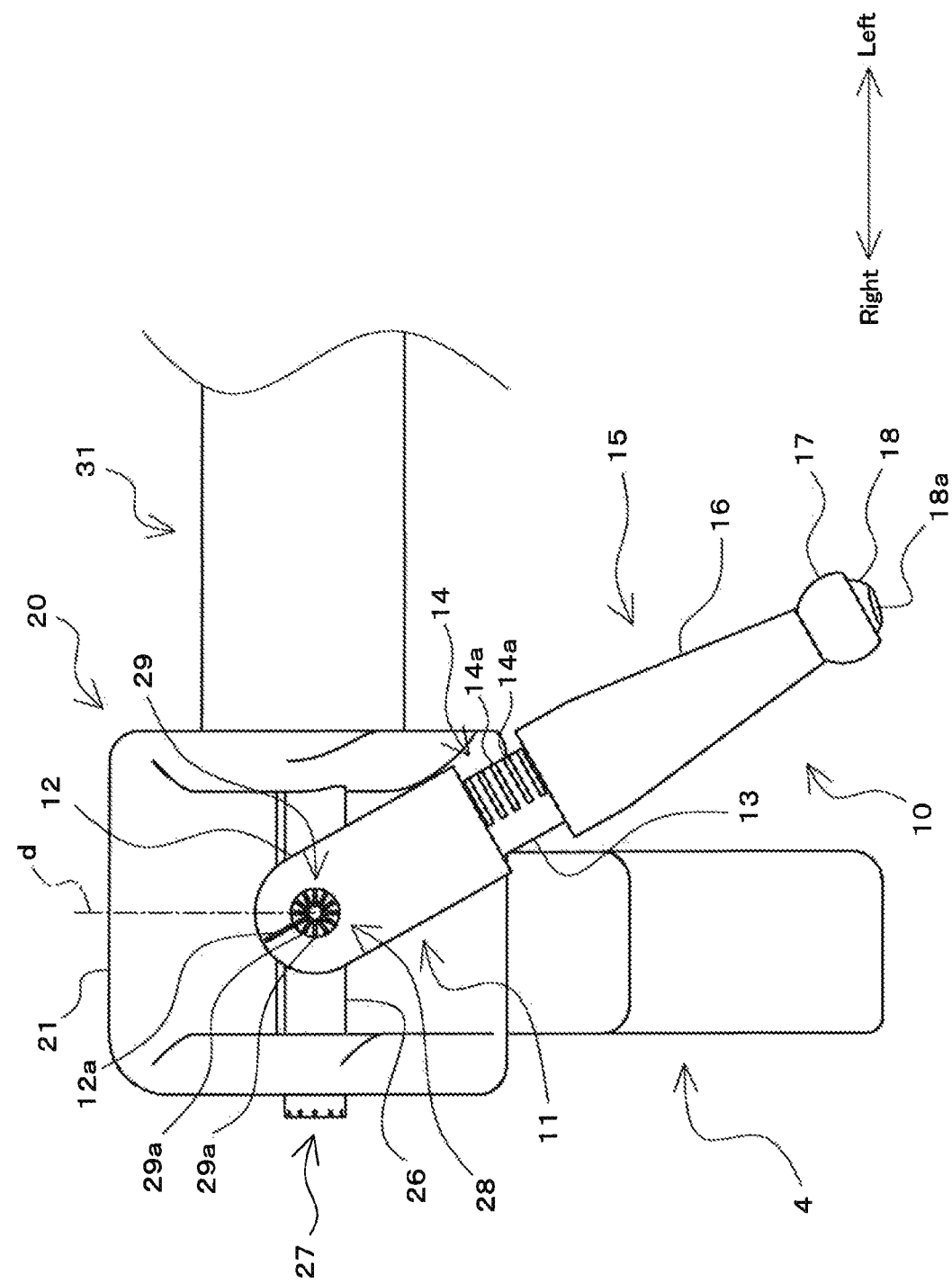
FIG. 4 is a diagram of the femoral head position determining instrument shown in FIG. 3, as viewed in the direction of arrow IV, in which the portion on the left side of the instrument is omitted.
Figure 5:
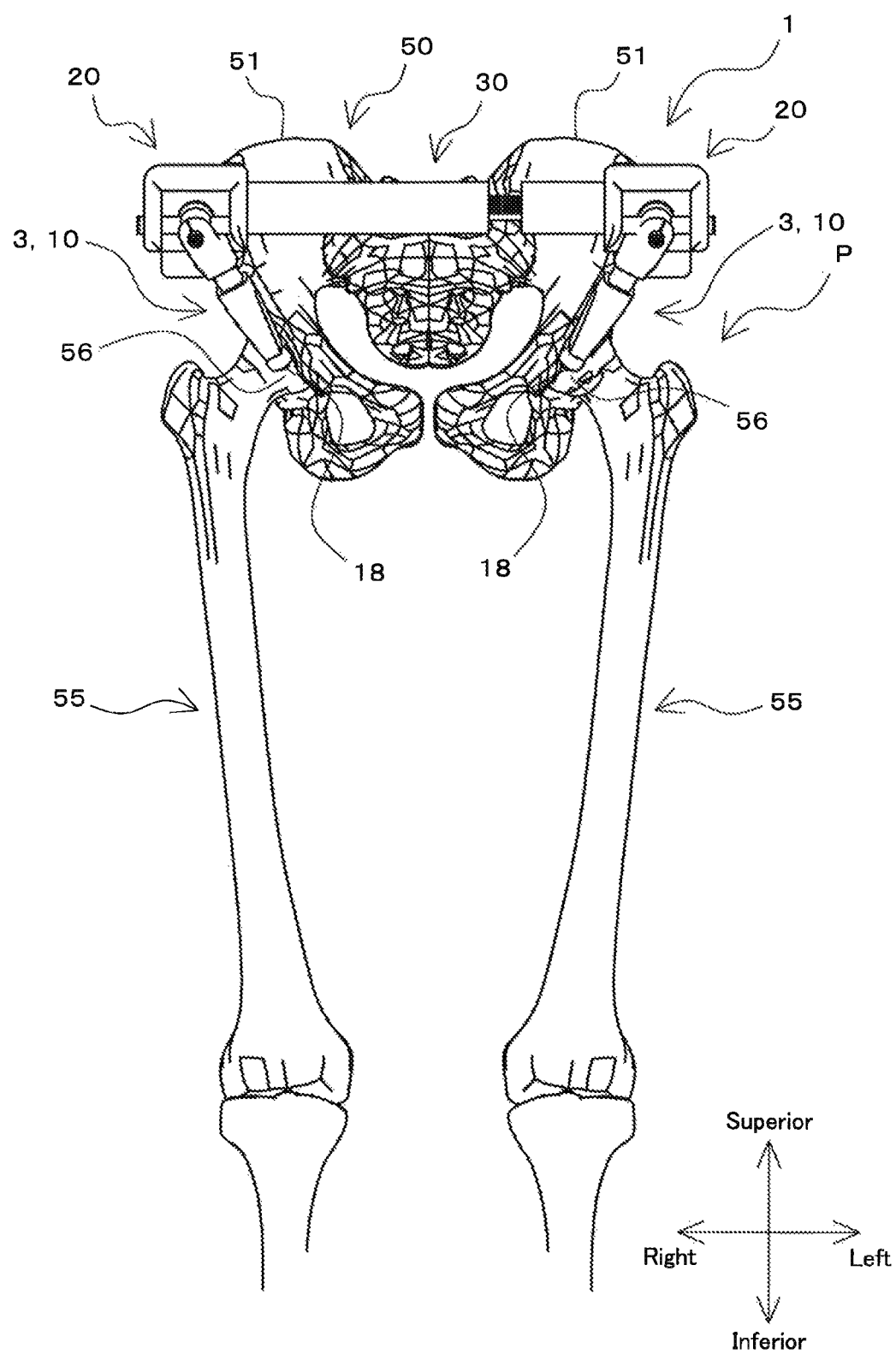
FIG. 5 is a diagram illustrating a state in which the femoral head position determining instrument shown in FIG. 1 is fixed to a patient, as viewed from the front side of the patient.
Figure 6:
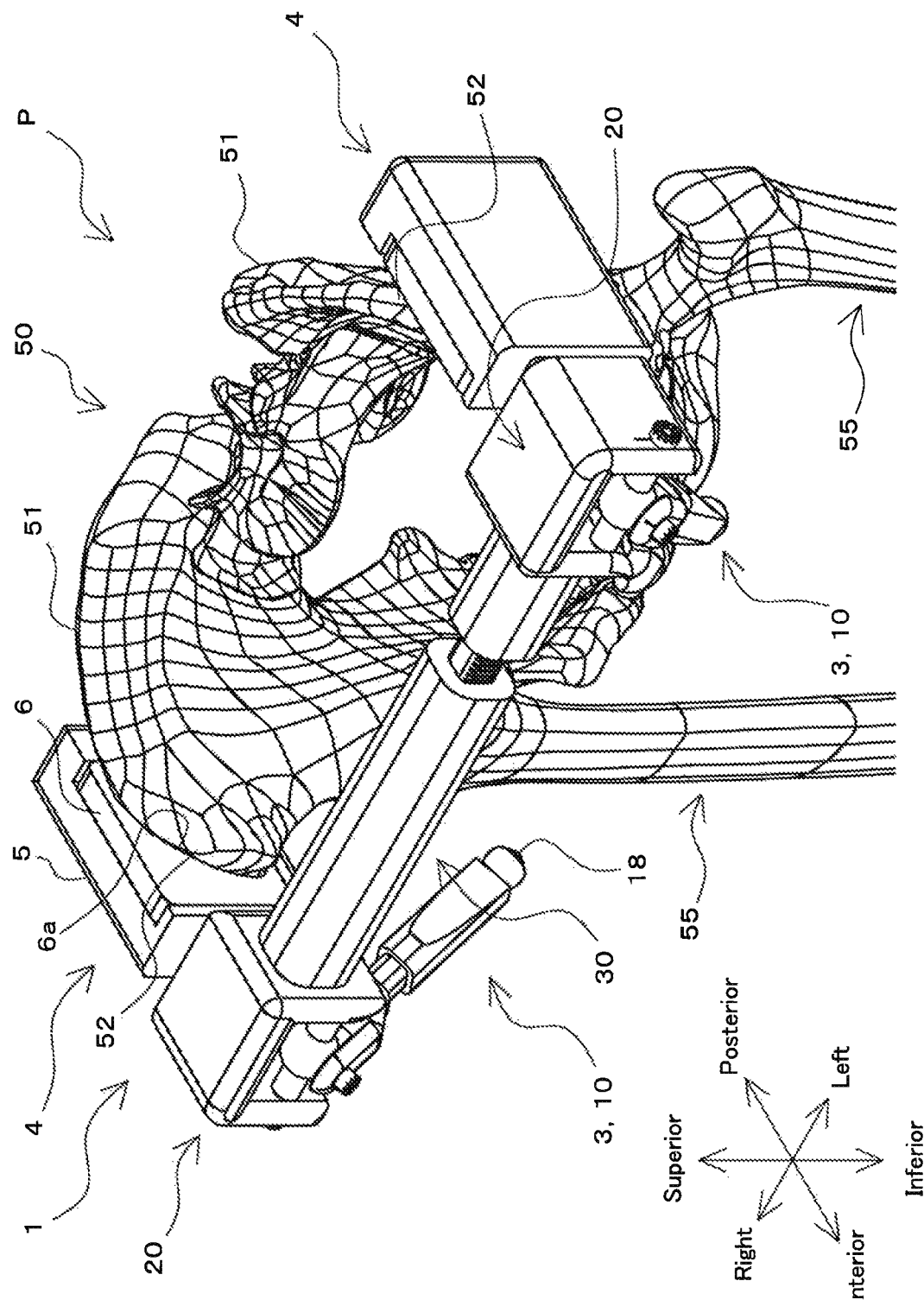
FIG. 6 is a perspective view of the femoral head position determining instrument in the state illustrated in FIG. 5.
Figure 7:
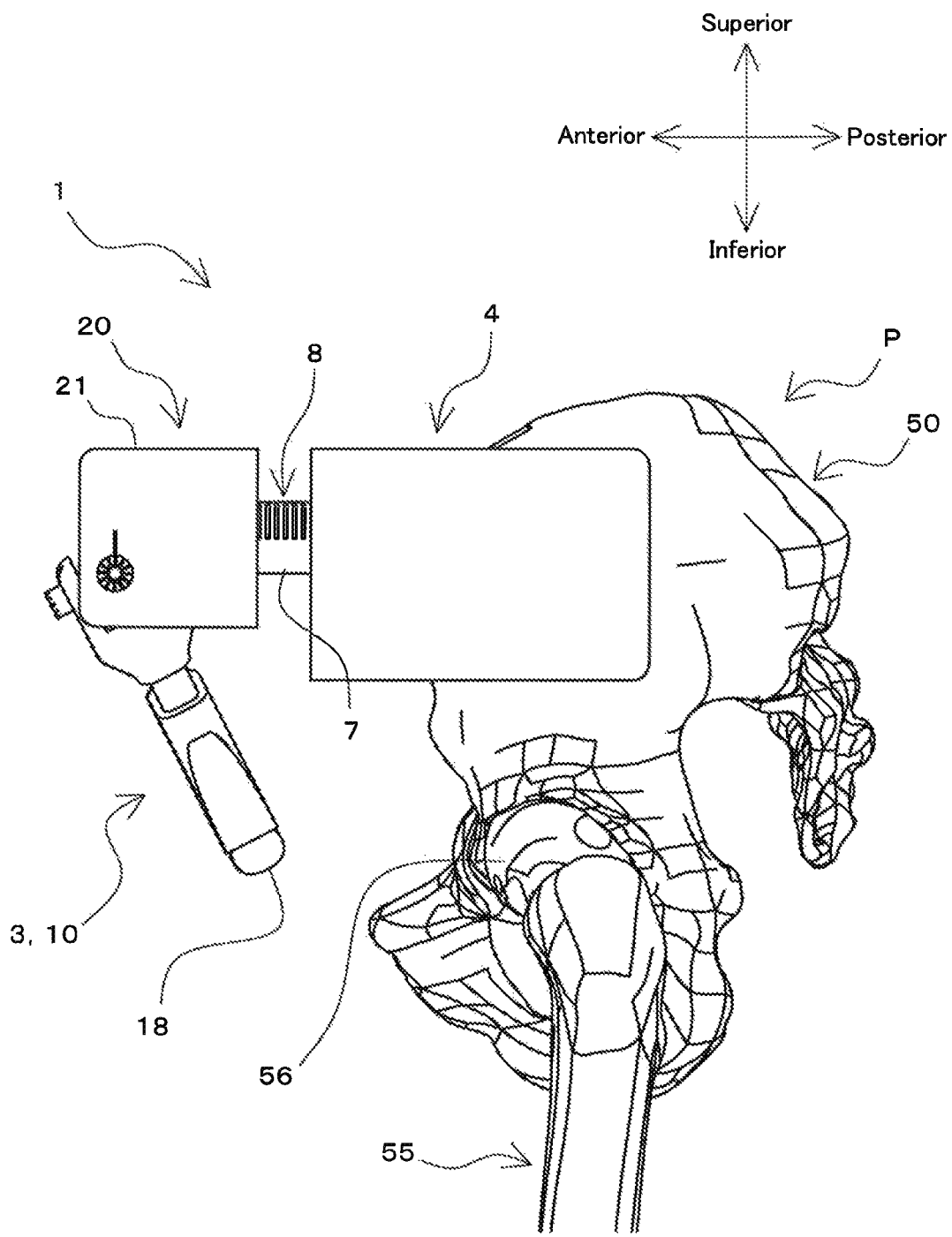
FIG. 7 is a diagram of the femoral head position determining instrument in the state illustrated in FIG. 5, as viewed from the lateral side of the patient.

FIGS. 1 to 4 are diagrams showing a configuration of a femoral head position determining instrument 1 (instrument for artificial knee joint replacement surgery) according to an embodiment of the present invention. FIG. 1 is a perspective view, FIG. 2 is a front view, FIG. 3 is a side view, and FIG. 4 is a diagram of the femoral head position determining instrument 1 shown in FIG. 3, as viewed in the direction of arrow IV, in which the portion on the left side of the instrument 1 is omitted. FIGS. 5 to 7 are diagrams illustrating a state in which the femoral head position determining instrument 1 is fixed to a patient P (only bones are shown). FIG. 5 is a front view, as viewed from the front side of the patient P, FIG. 6 is a perspective view, and FIG. 7 is a side view. It should be noted that in the figures, which will be described below, for the sake of ease of description, the direction indicated by the arrow "superior" is referred to as a superior side or a superior direction, the direction indicated by the arrow "inferior" is referred to as an inferior side or an inferior direction, the direction indicated by the arrow "anterior" is referred to as an anterior side or an anterior direction, the direction indicated by the arrow "posterior" is referred to as a posterior side or a posterior direction, the direction indicated by the arrow "right" is referred to as a right side, and the direction indicated by the arrow "left" is referred to as a left side. The vertical direction, the anteroposterior direction, and the horizontal direction in the figures correspond to the vertical direction, the anteroposterior direction, and the horizontal direction of a body of the patient P, respectively.

Figure 14B:
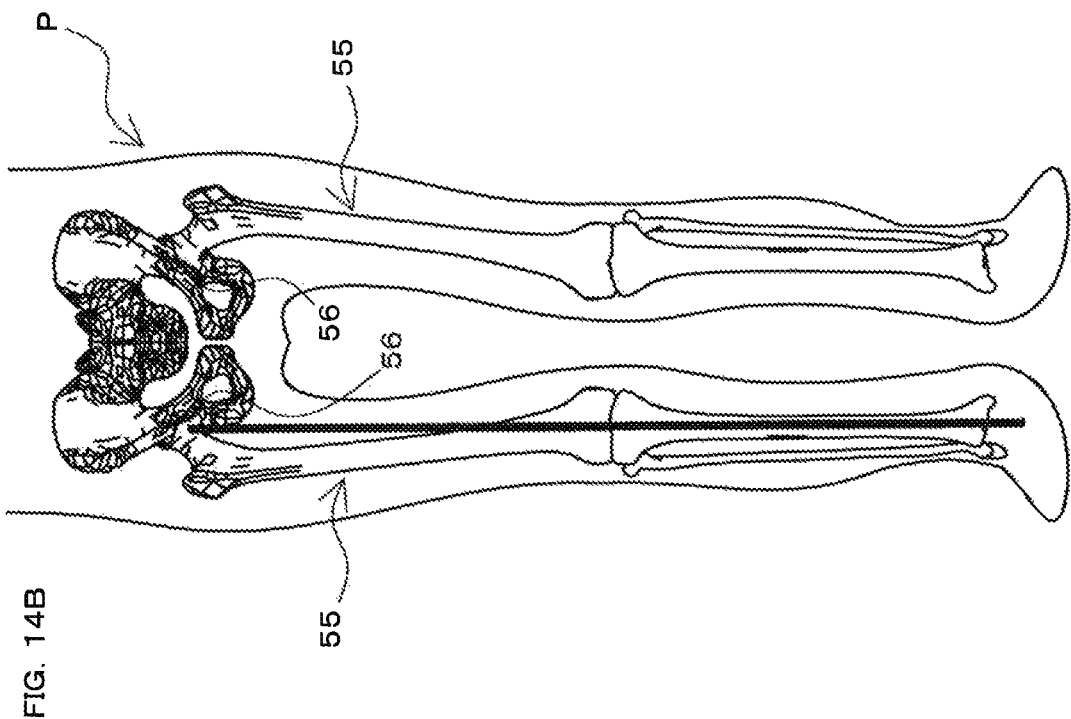
FIG. 14B is a diagram illustrating the state of the knee joint of the patient after artificial knee joint replacement surgery has been performed.
Figure 14A:
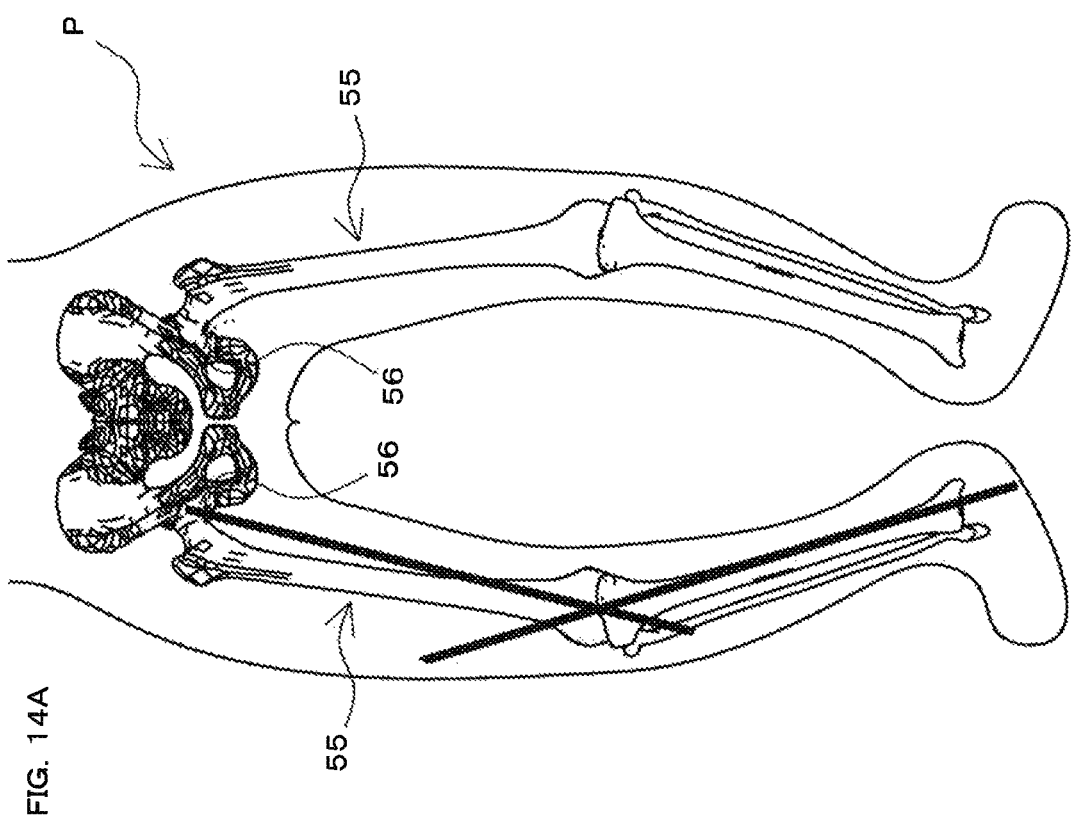
FIG. 14A is a diagram illustrating the state of the knee joint of the patient before artificial knee joint replacement surgery is performed.

The femoral head position determining instrument 1 according to this embodiment is used in artificial knee joint replacement surgery. Artificial knee joint replacement surgery is surgery in which a highly deformed knee joint of a patient suffering from knee osteoarthritis, chronic articular rheumatism, or the like, for example, is replaced by an artificial knee joint. FIG. 14A and FIG. 14B shows schematic views illustrating the state of a knee joint of a patient P before and after artificial knee joint replacement surgery is performed. FIG. 14A is a diagram illustrating the state of the knee joint of the patient P before artificial knee joint replacement surgery is performed, and FIG. 14B is a diagram illustrating the state of the knee joint of the patient P after artificial knee joint replacement surgery has been performed. As shown in FIG. 14A, in the patient P whose knee joint has deformed, the center of a head 56 of a femur 55, the knee joint center, and the second metatarsal bone are not aligned in a straight line. When artificial knee joint replacement surgery is performed on this patient P, the center of the head 56, the knee joint center, and the second metatarsal bone are aligned in a straight line, and thus the knee joint of the patient P can take on an appropriate state as shown in FIG. 14B. In the artificial knee joint replacement surgery, the distal end of the femur and the proximal end of the tibia in the knee joint of a patient are cut to appropriate cross sections, and then a femur-side implant and a tibia-side implant are provided on the respective cross sections.

When the distal end of the femur and the proximal end of the tibia are cut at appropriate positions and then the implants are provided on the respective cross sections after the cutting as described above, it is preferable that the center of the head 56 of the femur 55, the knee joint center, and the second metatarsal bone of the patient P are aligned in a straight line. However, since the femoral head 56 is located inside a human body, it is relatively difficult to confirm the position of the femoral head 56, and thus surgery is sometimes performed in a state in which the position of the femoral head 56 is not accurately understood. In such a case, the artificial knee joint is not provided in an appropriate manner.

In contrast, with the femoral head position determining instrument 1 according to this embodiment, the position of the femoral head center of the patient P can be relatively easily found, thus making it possible to provide the artificial knee joint in an appropriate manner. Hereinafter, the configuration of the femoral head position determining instrument 1 and a method of using the femoral head position determining instrument 1 will be described successively.

Overall Configuration

As shown in FIGS. 1 to 4, the femoral head position determining instrument 1 includes a holding mechanism 2 and an indicating mechanism 3.

The holding mechanism 2 includes a pair of holding portions 4, a pair of universal joint portions 20, and a connecting portion 30.

The two holding portions 4 have the same structure. Each of the holding portions 4 includes a contact plate attachment portion 5 (contact portion attachment portion) and a contact plate 6 (contact portion).

The contact plate attachment portion 5 is a portion that is formed in a substantially plate shape having a predetermined thickness in the horizontal direction and formed in a rectangular shape as viewed in the horizontal direction. An accommodating recessed portion 5a is formed in one surface of the contact plate attachment portion 5 in the thickness direction. This accommodating recessed portion 5a is formed in a recessed shape to accommodate the contact plate 6. The accommodating recessed portion 5a is formed on the inner surface of each of the pair of contact plate attachment portions 5 that are provided facing each other. The accommodating recessed portion 5a is formed so as to be open upward and inward in the femoral head position determining instrument 1.

A hole portion (not shown) extending from the surface on the anterior side of the contact plate attachment portion 5 toward the posterior side is formed in the contact plate attachment portion 5, and a rod-shaped portion 7 that is formed in one piece with a box portion 21 of the universal joint portion 20, which will be described in detail later, is inserted into the hole portion (see FIG. 3). It should be noted that, although not shown in the figures, the femoral head position determining instrument 1 includes a fixing mechanism for fixing the rod-shaped portion 7 to the contact plate attachment portion 5. An example of this fixing mechanism is a mechanism using a screw, a ball plunger, or the like, but there is no limitation thereto, and another configuration may be possible.

The contact plate 6 is a member formed in a plate shape having a size and a thickness smaller than those of the contact plate attachment portion 5. The length in the vertical direction, the length in the horizontal direction, and the thickness in the anteroposterior direction of the contact plate 6 are substantially the same as the length in the vertical direction, the length in the horizontal direction, and the thickness in the anteroposterior direction of the accommodating recessed portion 5a, respectively. Accordingly, the contact plate 6 can be attached to and detached from the accommodating recessed portion 5a of the contact plate attachment portion 5.

A recessed portion 6a for a pelvis (recessed portion for a contact target) is formed in the surface on one side of the contact plate 6. The recessed portion 6a for a pelvis is formed in a curved thin groove shape. The contact plate 6 is accommodated in the contact plate attachment portion 5 and fixed such that the recessed portion 6a for a pelvis faces inward.

The contact plate 6 is tailored to the patient P on whom surgery is to be performed. Specifically, the contact plate 6 is formed in a shape that allows the recessed portion 6a to be fitted to an anterior superior iliac spine 52 of the patient P (a portion extruding outward in the horizontal direction in an ilium 51 of a pelvis 50 of the patient P; see FIG. 6) in a state in which the femoral head position determining instrument 1 is attached to the patient P (see FIG. 5 etc.). More specifically, the recessed portion 6a for a pelvis of the right contact plate 6 is formed in a shape that is fitted to the right anterior superior iliac spine 52 of the patient P, whereas the recessed portion 6a for a pelvis of the left contact plate 6 is formed in a shape that is fitted to the left anterior superior iliac spine 52 of the patient P. Accordingly, the femoral head position determining instrument 1 can be fitted to the patient P.

It should be noted that, although not shown in FIGS. 1 to 4 etc., the holding portion 4 includes a fixing mechanism for fixing the contact plate 6 accommodated in the accommodating recessed portion 5a of the contact plate attachment portion 5 to the contact plate attachment portion 5. An example of this fixing mechanism is a mechanism using a screw, a claw-shaped portion, or the like to fix the contact plate 6 to the contact plate attachment portion 5, but there is no limitation thereto, and another configuration may be possible.

The indicating mechanism 3 includes a pair of extension portions 10. The two extension portions 10 have the same structure. Each of the extension portion 10 is provided such that the base end is rotatably attached to the holding portion 4 via the universal joint portion 20, whereas the front end extends in the direction away from the holding portion 4. The extension portion 10 includes a base end portion 11 that is a portion located on the base end side and a front end portion 15 that is a portion located on the front end side.

The base end portion 11 includes a base portion 12 and a rod-shaped portion 13, and the base portion 12 and the rod-shaped portion 13 are formed in one piece.

The base portion 12 is a portion that functions as a yoke portion of the universal joint portion 20, which will be described in detail later. The base portion 12 is rotatable about a first shaft portion 26, acting as an axial center, of the universal joint portion 20, and is also rotatable relative to a second shaft portion 28, acting as an axial center, of the universal joint portion 20 about the second shaft portion 28.

The rod-shaped portion 13 is a portion having a rod shape in which one end is formed in one piece with the base portion 12. The rod-shaped portion 13 is formed such that the lateral cross section has a substantially rectangular shape. Segmented indicator lines 14a extending in a direction orthogonal to the longitudinal direction of the rod-shaped portion 13 are provided on the lateral surface of the rod-shaped portion 13 at equal intervals in the longitudinal direction of the rod-shaped portion 13. An extension portion indicator 14 serving as an index of the length of the extension portion 10 is configured by these indicator lines 14a. The rod-shaped portion 13 is inserted through a hole portion (not shown) formed in the front end portion 15 of the extension portion 10.

The front end portion 15 is provided to be capable of being slid and moved in the longitudinal direction of the rod-shaped portion 13. The front end portion 15 includes a sliding portion 16 and a bowl-shaped portion 17.

The sliding portion 16 is a portion formed in a substantially elongated tubular shape. The rod-shaped portion 13 is inserted into the hole portion formed inside the sliding portion 16. In the extension portion 10, the sliding portion 16 is slid and moved in the longitudinal direction of the rod-shaped portion 13 while the inner circumferential surface of the sliding portion 16 slides on the outer circumferential surface of the rod-shaped portion 13. Accordingly, the extension portion 10 can be elongated and shortened in the longitudinal direction. It should be noted that, although not shown in the figures, the extension portion 10 is provided with a fixing mechanism, and a state in which the front end portion 15 is fixed to the base end portion 11 and a state in which the fixation of the front end portion 15 to the base end portion 11 is released can be switched as necessary. The fixing mechanism can be configured by using a screw, a ball plunger, or the like, for example.

The bowl-shaped portion 17 is formed in a bowl shape such as a shape obtained by cutting off half of a hollow sphere, and its opening portion is open in a direction in which the sliding portion 16 extends. The bowl-shaped portion 17 is fixed to the front end portion of the sliding portion 16.

A ball-shaped member that cannot be released from the bowl-shaped portion 17 and that is rotatable relative to the bowl-shaped portion 17 is accommodated in the bowl-shaped portion 17. This ball-shaped member is provided as a head position indicating portion 18 (position identification target indicating portion) that indicates a position corresponding to the position of the femoral head 56 of the patient P in a state in which the femoral head position determining instrument 1 is attached to the patient P. An attachment hole portion 18a to which the front end portion of an alignment rod 60, which will be described in detail later, is attached is formed in this head position indicating portion 18. The attachment hole portion 18a is exposed from the opening portion of the bowl-shaped portion 17.

The two universal joint portions 20 have the same structure. Each of the universal joint portions 20 includes the box portion 21, the first shaft portion 26, the second shaft portion 28, and the base portion 12 of the extension portion 10 described above.

The box portion 21 includes four wall portions 22, 23, 24, and 25 formed in a square shape in a plan view, and these wall portions are formed in one piece. Specifically, as shown in FIG. 1 etc., the box portion 21 includes the upper wall portion 22, the posterior wall portion 23, the inner wall portion 24, and the outer wall portion 25, and these wall portions are formed in one piece. That is, the box portion 21 is shaped in a substantially box shape in which the lower side and the anterior side are open. The holding portion 4 is attached to the posterior wall portion 23 via the rod-shaped portion 7 (see FIG. 3), and the connecting portion 30 is fixed to the inner wall portion 24. It should be noted that, out of the wall portions constituting the box portion 21, the inner wall portion 24 is a wall portion located on a side where the connecting portion 30 is provided, and, out of the wall portions constituting the box portion 21, the outer wall portion 25 is a wall portion located on a side opposite to the side where the connecting portion 30 is provided.

The above-described rod-shaped portion 7 is formed in one piece with the posterior wall portion 23. The rod-shaped portion 7 is formed to extend from the posterior wall portion 23 toward the posterior side, and its front end portion is inserted through the hole portion formed in the contact plate attachment portion 5 of the holding portion 4. This hole portion can be slid and moved relative to the rod-shaped portion 7 in the longitudinal direction of the rod-shaped portion 7. Accordingly, a gap G (see FIG. 3) between the holding portion 4 and the universal joint portion 20 can be adjusted.

Segmented indicator lines 8a extending in a direction orthogonal to the longitudinal direction of the rod-shaped portion 7 are provided on the lateral surface of the rod-shaped portion 7 at equal intervals in the longitudinal direction of the rod-shaped portion 7. A gap indicator 8 serving as an index of the length of the gap G between the holding portion 4 and the universal joint portion 20 is configured by these indicator lines 8a.

The first shaft portion 26 is a shaft portion that is provided to extend in the horizontal direction and to be rotatable relative to the inner wall portion 24 and the outer wall portion 25 of the box portion 21. The outer end portion of the first shaft portion 26 is provided to project outward from the outer wall portion 25. A first angle indicator 27 is formed on a surface of this portion that can be seen from the outside. This first angle indicator 27 is used to find the angle (also referred to as "first angle" hereinafter) of the extension portion 10 with respect to the vertical direction, as viewed in the horizontal direction. Specifically, with reference to FIG. 3, when the extension portion 10 is rotated relative to the box portion 21 about the first shaft portion 26 as a central axis, the first angle indicator 27 is also rotated relative to the box portion 21 with the rotation of the extension portion 10. An angle position (not shown) provided on an indicator line 27a of the first angle indicator 27 that is aligned with a first angle indicator line 25a formed on the outer wall portion 25 of the box portion 21 is taken as the first angle of the extension portion 10.

It should be noted that, although not shown in the figures, the universal joint portion 20 includes a fixing mechanism for fixing the extension portion 10, which is rotated about the first shaft portion 26 as a central axis, at the first angle position. An example of the configuration of the fixing mechanism is a configuration in which a ball portion of a ball plunger (not shown) is fitted into any of a plurality of recessed portions (not shown) arranged in an annular manner along the outer circumferential surface of the first shaft portion 26. However, the configuration of the fixing mechanism is not limited thereto and may be configured by using a screw or the like, for example.

The second shaft portion 28 is a shaft portion that is provided to extend in a direction orthogonal to the first shaft portion 26 and is fixed to the first shaft portion 26. The extension portion 10 is provided to be rotatable relative to the second shaft portion 28 about the central axis of the second shaft portion 28. As shown in FIG. 4, a second angle indicator 29 is formed on a portion of the second shaft portion 28 that is exposed to the outside with respect to the extension portion 10. This second angle indicator 29 is used to find the angle (also referred to as "second angle" hereinafter) of the extension portion 10 with respect to a direction d that is orthogonal to both the central axis of the first shaft portion 26 and the central axis of the second shaft portion 28, as viewed in the axial direction of the second shaft portion 28. Specifically, with reference to FIG. 4, when the extension portion 10 is rotated about the second shaft portion 28 as a central axis, an angle position (not shown) provided on an indicator line 29a of the second angle indicator 29 that is aligned in a straight line with a second angle indicator line 12a formed on the base portion 12 of the extension portion 10 is taken as the second angle of the extension portion 10.

It should be noted that, although not shown in the figures, the universal joint portion 20 includes a fixing mechanism for fixing the extension portion 10, which is rotated about the second shaft portion 28 as a central axis, at the second angle position. An example of the configuration of the fixing mechanism is a configuration in which a ball portion of a ball plunger (not shown) is fitted into any of a plurality of recessed portions (not shown) arranged in an annular manner along the outer circumferential surface of the second shaft portion 28. However, the configuration of the fixing mechanism is not limited thereto and may be configured by using a screw or the like, for example.

The connecting portion 30 connects the pair of holding portions 4 by connecting the pair of box portions 21 in a state in which the distance between the pair of holding portions 4 is maintained. The connecting portion 30 includes a right portion 31 and a left portion 35.

The right portion 31 is a portion formed in a substantially tubular shape extending in the horizontal direction. The right end portion of the right portion 31 is formed in one piece with the inner wall portion 24 of the right box portion 21. A rod-shaped portion 37 of the left portion 35, which will be described in detail later, is fitted into the inner circumferential surface of the right portion 31.

The left portion 35 includes a base portion 36 and the rod-shaped portion 37, and the base portion 36 and the rod-shaped portion 37 are formed in one piece. The base portion 36 is a portion formed in a columnar shape extending in the horizontal direction. The length of the base portion 36 in the horizontal direction is shorter than the length of the right portion 31 in the horizontal direction.

The rod-shaped portion 37 is a portion that has a rod shape of which one end portion is formed in one piece with the base portion 36. The rod-shaped portion 37 is formed such that the lateral cross section has a substantially rectangular shape. Segment indicator lines 38a extending in a direction orthogonal to the longitudinal direction of the rod-shaped portion 37 are provided on the lateral surface of the rod-shaped portion 37 at equal intervals in the longitudinal direction of the rod-shaped portion 37. A connecting portion indicator 38 serving as an index of the length of the connecting portion 30 is configured by these indicator lines 38a. The rod-shaped portion 37 is fitted into the inner circumferential surface of the right portion 31.

The connecting portion 30 having the above-described configuration can be extended and shortened in the longitudinal direction by sliding one of the right portion 31 and the left portion 35 relative to the other in the horizontal direction. It should be noted that, although not shown in the figures, the connecting portion 30 is provided with a fixing mechanism, and a state in which the right portion 31 and the left portion 35 are fixed and a state in which the fixation of the right portion 31 and the left portion 35 relative to each other is released can be switched as necessary. The fixing mechanism can be configured by using a screw, a ball plunger, or the like, for example.

Usage Method

In order to use the femoral head position determining instrument 1 according to this embodiment, first, the contact plates 6 are tailored to the patient P on whom surgery is to be performed. Specifically, first, the shapes of the bones near the pelvis of the patient P are modeled using X-rays, MRI (magnetic resonance imaging), 3D-CT (3 dimensional-computed tomography), or the like. Based on this model, the recessed portion 6a for a pelvis having a shape that is complementary to the shape of the anterior superior iliac spine 52 on the right side of the patient P is formed in one of the contact plates 6, whereas the recessed portion 6a for a pelvis having a shape that is complementary to the shape of the anterior superior iliac spine 52 on the left side of the patient P is formed in the other of the contact plates 6. The contact plates 6 formed in this manner are respectively accommodated in the accommodating recessed portions 5a of the corresponding contact plate attachment portions 5 and fixed.

Next, an operator fixes the femoral head position determining instrument 1 equipped with the contact plates 6 formed as described above to the patient P. Specifically, the operator adjusts the length of the femoral head position determining instrument 1 in the horizontal direction such that the anterior superior iliac spine 52 on the right side of the patient P is fitted into the recessed portion 6a for a pelvis of the right contact plate 6, and the anterior superior iliac spine 52 on the left side of the patient P is fitted into the recessed portion 6a for a pelvis of the left contact plate 6. At this time, the operator slides, in the horizontal direction, one of the portions 31 and 35 in the horizontal direction of the connecting portion 30 relative to the other of the portions 35 and 31 as appropriate, holds the anterior superior iliac spines 52 on both sides of the patient P between the pair of holding portions 4, and then fixes the above-mentioned portions 31 and 35 of the connecting portion 30 relative to each other using the fixing mechanism. Accordingly, the holding mechanism 2 can be fixed to the patient P.

It should be noted that, at this time, the operator can compare the length of the connecting portion 30 indicated by the connecting portion indicator 38 with the shapes of the bones of the patient that has been modeled using X-rays etc., or the like. That is, the operator can use the connecting portion indicator 38 for confirmation. When the holding mechanism 2 is fixed to the patient P as described above, the gaps G between the holding portions 4 and the universal joint portions 20 are adjusted based on the size and the shape of the abdominal region of the patient, and thus the femoral head position determining instrument 1 can be fixed to the patient P without interference from the abdominal region of the patient P.

Next, the operator arranges the head position indicating portions 18 provided at the front end portions of the extension portions 10 at the positions of the femoral heads 56 of the patient P, as viewed from the front side of the patient P. Specifically, the operator adjusts the first angles, the second angles, the gaps G, and the lengths of the extension portions 10 based on the positional relationship between the anterior superior iliac spines 52 and the femoral heads 56 of the patient P that was obtained in advance through modeling of the shapes of bones of the patient, and thus arranges the head position indicating portions 18 at the positions of the femoral heads 56. At this time, the operator can accurately adjust the first angles, the second angles, the gaps G, and the lengths of the extension portions 10 described above while checking the indicators 8, 14, 27, and 29, and therefore, the head position indicating portions 18 can be accurately arranged at the positions of the femoral heads 56.

Next, the operator attaches the front end portion of the alignment rod 60 to the attachment hole portion 18a of the head position indicating portion 18 arranged at a position corresponding to the position of the femoral head 56 as described above.

Figure 8:
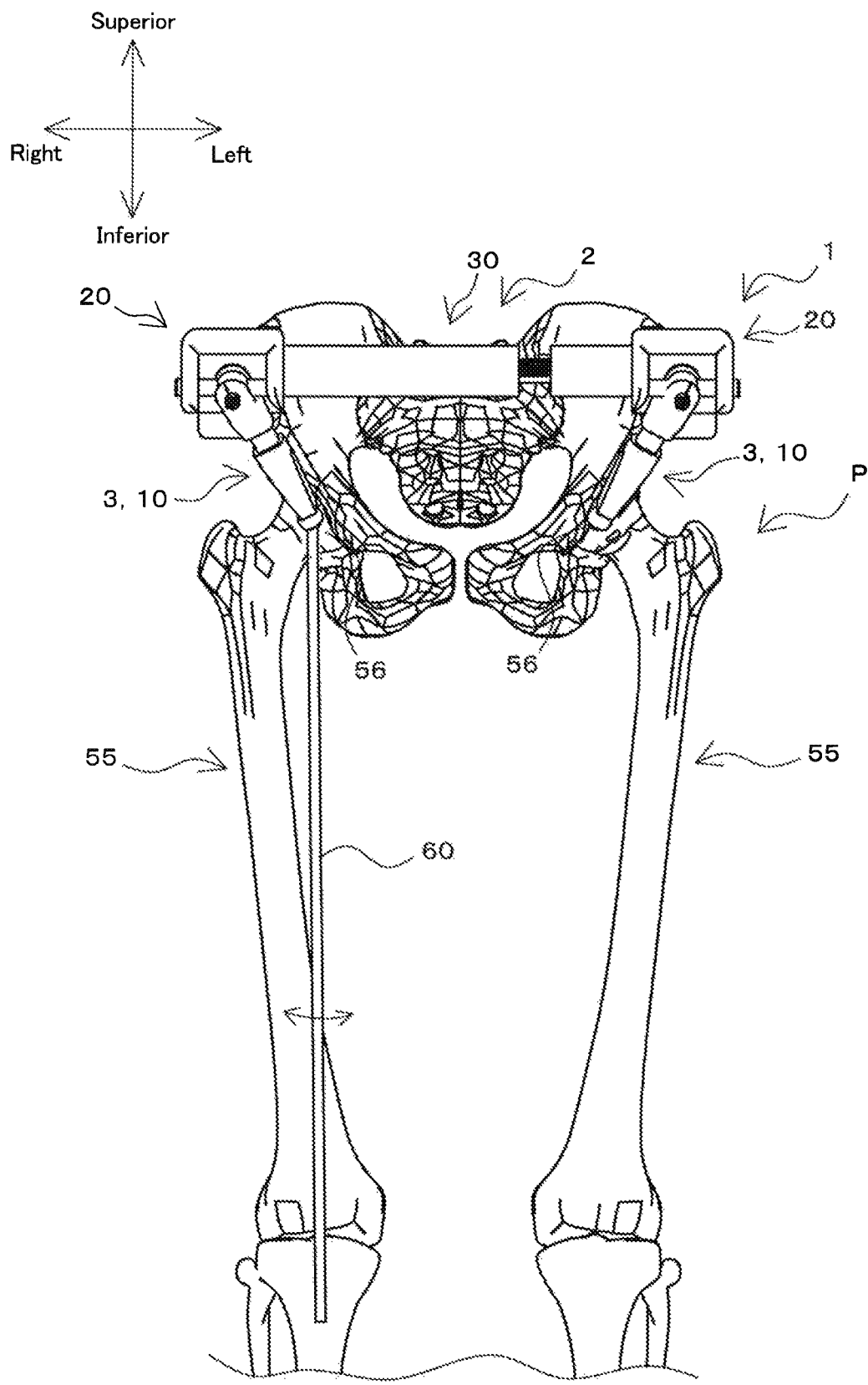
FIG. 8 is a diagram of the femoral head position determining instrument in the state illustrated in FIG. 5, as viewed from the front side of the patient, and illustrates a state in which an alignment rod is attached to the femoral head position determining instrument.

Accordingly, the operator can confirm the alignment while changing the orientation of the alignment rod 60 about the head position indicating portion 18 as the center (see FIG. 8).

The operator can determine the positions of cross sections of the knee joint (specifically, the distal end of the femur and the proximal end of the tibia) such that the femoral head center, the knee joint center, and the second metatarsal bone of the patient are aligned in a straight line after the artificial knee joint has been attached, while confirming the alignment as described above. Accordingly, the cross sections on which the artificial knee joint is provided can be formed appropriately.

Effects

As described above, with the femoral head position determining instrument 1 according to this embodiment, the head position indicating portions 18 are arranged at positions corresponding to the femoral heads 56 in a state in which the contact plates 6 are in contact with the anterior superior iliac spines 52 of a patient. At this time, the head position indicating portions 18 are arranged based on the relative positional relationship between the anterior superior iliac spines 52 and the femoral heads 56 of the patient P that was obtained through modeling of the shapes of the bones of the patient P using X-rays or the like. Accordingly, the head position indicating portions 18 can be accurately arranged at positions corresponding to the femoral heads 56. The operator who is to perform artificial knee joint replacement surgery can directly and visually observe the head position indicating portions 18 arranged as described above and thus easily find the positions of the femoral heads 56 of the patient.

Therefore, with the femoral head position determining instrument 1, the positions of the femoral heads 56 of the patient P can be easily identified. In addition, the positions of the head position indicating portions 18 determined as described above accurately correspond to the positions of the femoral heads 56, and thus alignments can be obtained with high accuracy.

Also, with the femoral head position determining instrument 1, the recessed portions 6a for a pelvis into which the anterior superior iliac spines 52 are fitted are formed in the contact plates 6, and the contact plates 6 can hold the patient P in close contact.

Also, with the femoral head position determining instrument 1, the contact plates 6 in which the recessed portions 6a for a pelvis corresponding to the shapes of the anterior superior iliac spines 52 of the patient P are formed are brought into contact with the anterior superior iliac spines 52 of the patient P. Accordingly, the contact plates 6 can hold the patient P in closer contact.

Also, with the femoral head position determining instrument 1, the contact plates 6 are manufactured based on the anterior superior iliac spines 52 of the patient P, but other portions (portions other than the contact plates 6 in the femoral head position determining instrument 1) need not be changed depending on the patient P. That is, with the femoral head position determining instrument 1, a small number of parts are manufactured depending on the patient P, and therefore, an instrument appropriate for the patient P can be prepared at low cost and in a short period of time.

Also, with the femoral head position determining instrument 1, the recessed portions 6a for a pelvis of the contact plates 6 are formed based on the shapes of the anterior superior iliac spines 52 of the patient P. Accordingly, the contact plates 6 are customized based on the shapes of the anterior superior iliac spines 52 of the patient P on whom surgery is to be performed, and therefore, the contact plates 6 can hold the patient P in even closer contact.

Also, with the femoral head position determining instrument 1, if the contact plates 6 are manufactured according to the patient P are stored, the femoral head position determining instrument 1 can be reused in a case where the patient P needs to undergo revision surgery.

Also, with the femoral head position determining instrument 1, the anterior superior iliac spines 52 of the patient P are held between the pair of holding portions 4, and thus the instrument 1 can be easily fixed to the patient P.

Also, with the femoral head position determining instrument 1, the alignment rods 60 for confirming alignment (alignment in which the femoral head center, the knee joint center, and the second metatarsal bone center are aligned in a straight line) that is important during artificial knee joint replacement surgery can be appropriately arranged on the patient P. Specifically, the operator can confirm the alignment in a state in which the alignment rod 60 is attached to the attachment hole portion 18a of the head position indicating portion 18, that is, one end portion of the alignment rod 60 is fixed at a position corresponding to the position of the femoral head 56. Accordingly, appropriate alignment in which the position of the femoral head 56 is accurately reflected can be confirmed.

Also, with the femoral head position determining instrument 1, the head position indicating portions 18 are rotatable relative to the bowl-shaped portions 17, and therefore, the operator can easily change the orientation of the alignment rod 60 in the state in which the end portion of the alignment rod 60 is attached to the attachment hole portion 18a of the head position indicating portion 18.

Also, with the femoral head position determining instrument 1, after the artificial knee joint is attached to the knee joint of the patient P, one end portion of the alignment rod 60 is attached to the attachment hole portion 18a and the orientation of the alignment rod 60 is changed, thus making it easy to confirm that the center of the femoral head 56, the knee joint center, and the second metatarsal bone of the patient P are aligned in a straight line.

Also, with the femoral head position determining instrument 1, the head position indicating portions 18 are arranged at positions corresponding to the positions of the femoral heads 56 based on the positional relationship between the anterior superior iliac spines 52 and the femoral heads 56 that was obtained in advance prior to the surgery in a state in which the contact plates 6 of the holding portions 4 are in contact with the anterior superior iliac spines 52. Here, the anterior superior iliac spines 52 are portions of the pelvis 50 that protrude laterally and are covered with only a very thin layer (e.g., skin). That is, the relative positional relationship between the contact plates 6 brought into contact with the anterior superior iliac spines 52 via these thin layers and the head position indicating portions 18 is substantially the same as the previously obtained relative positional relationship between the anterior superior iliac spines 52 and the femoral heads 56. Accordingly, a large positional difference between the positions of the head position indicating portions 18 and the actual positions of the femoral heads 56 can be prevented. Therefore, with the femoral head position determining instrument 1, the positions of the femoral heads 56 can be accurately understood.

Also, with the femoral head position determining instrument 1, the front ends of the extension portions 10 of the indicating mechanism 3, the extension portions 10 being formed to extend from the base end side toward the front end side, indicate the positions of the femoral heads 56. Accordingly, the head position indicating portions 18 can be arranged at positions corresponding to the positions of the femoral heads 56 that are positionally separated from the anterior superior iliac spines 52 as the contact targets.

Also, with the femoral head position determining instrument 1, the positions of the front end portions 15 relative to the positions of the base end portions 11 of the extension portions 10 can be easily adjusted by moving the front end portions 15 relative to the base end portion 11. Accordingly, the positions of the head position indicating portions 18 can be adjusted appropriately.

Also, with the femoral head position determining instrument 1, the base end portions 11 of the extension portions 10 can be rotated relative to the holding mechanism 2 by using the universal joint portions 20, and thus the orientation of the extension portions 10 can be easily adjusted. Accordingly, the positions of the head position indicating portions 18 can be adjusted appropriately.

Although an embodiment of the present invention has been described thus far, the present invention is not limited to the above-described embodiment, and various modifications can be made within the scope recited in the claims. For example, the following modifications are possible.

Figure 9:
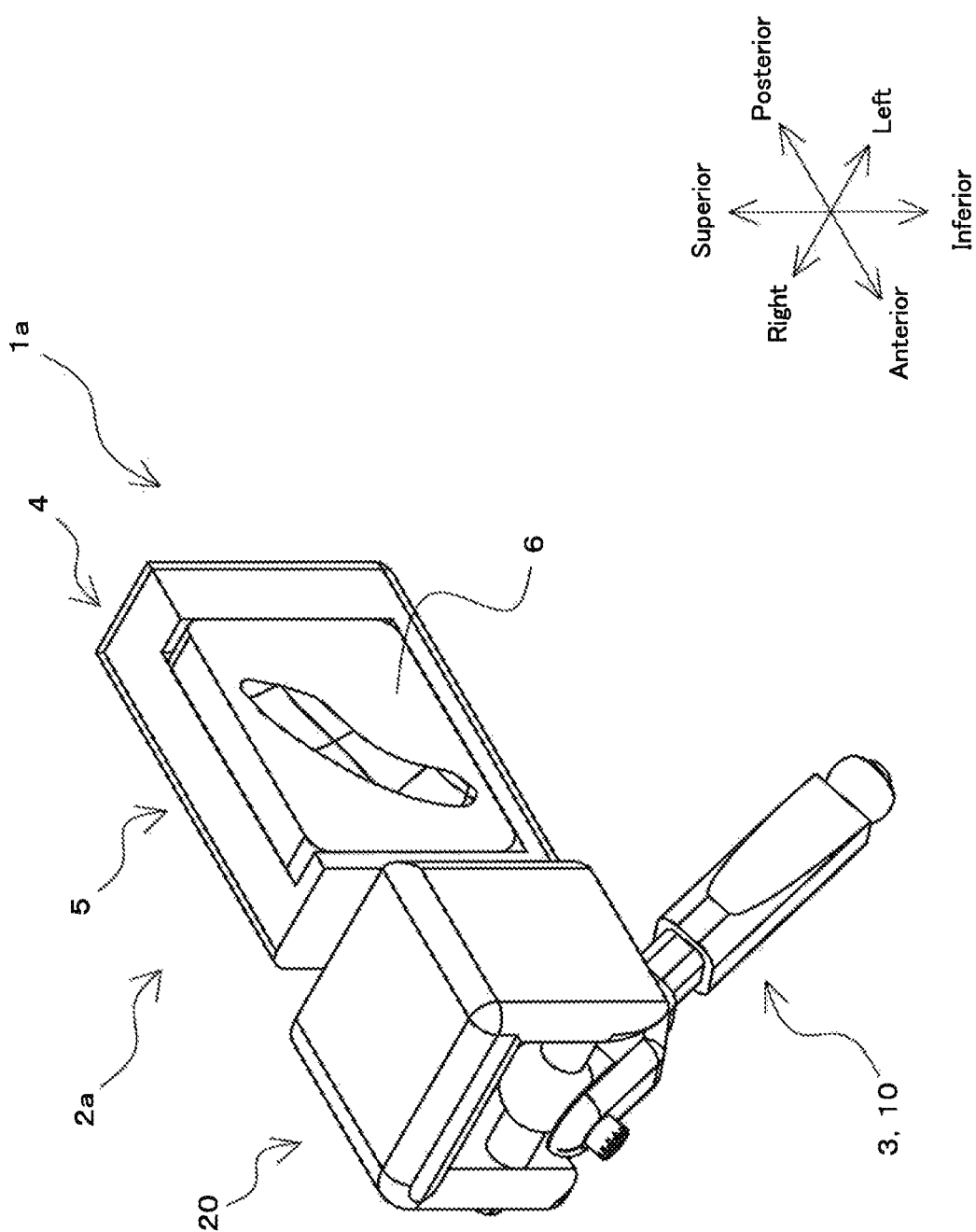
FIG. 9 is a perspective view of a femoral head position determining instrument according to a modified example.

Modified Examples (1) FIG. 9 is a perspective view of a femoral head position determining instrument 1*a* according to a modified example. With the femoral head position determining instrument 1 according to the above-described embodiment, the anterior superior iliac spines 52 of the patient P are held between the pair of holding portions 4 from both sides, and thus the instrument 1 is fixed to the patient P, but there is no limitation thereto. For example, as shown in FIG. 9, the femoral head position determining instrument 1*a* including a holding mechanism 2*a* having one holding portion 4 can be configured. This femoral head position determining instrument 1*a* is used in a state in which the contact plate 6 of the holding portion 4 is in contact with either of the anterior superior iliac spines 52 of the patient P and supported by an operator or an assistant (or supported by a separate supporting instrument). With this femoral head position determining instrument 1*a*, work including the operator supporting the femoral head position determining instrument 1*a*, or support using a separate instrument is required while the femoral head position determining instrument 1*a* is used, but the configuration can be made significantly simple and the size of a product can be made smaller compared with the above-described femoral head position determining instrument 1. Specifically, unlike the above-described femoral head position determining instrument 1, one of the holding portions 4, one of the extension portions 10, the connecting portion 30, and the like can be omitted.

Figure 10:
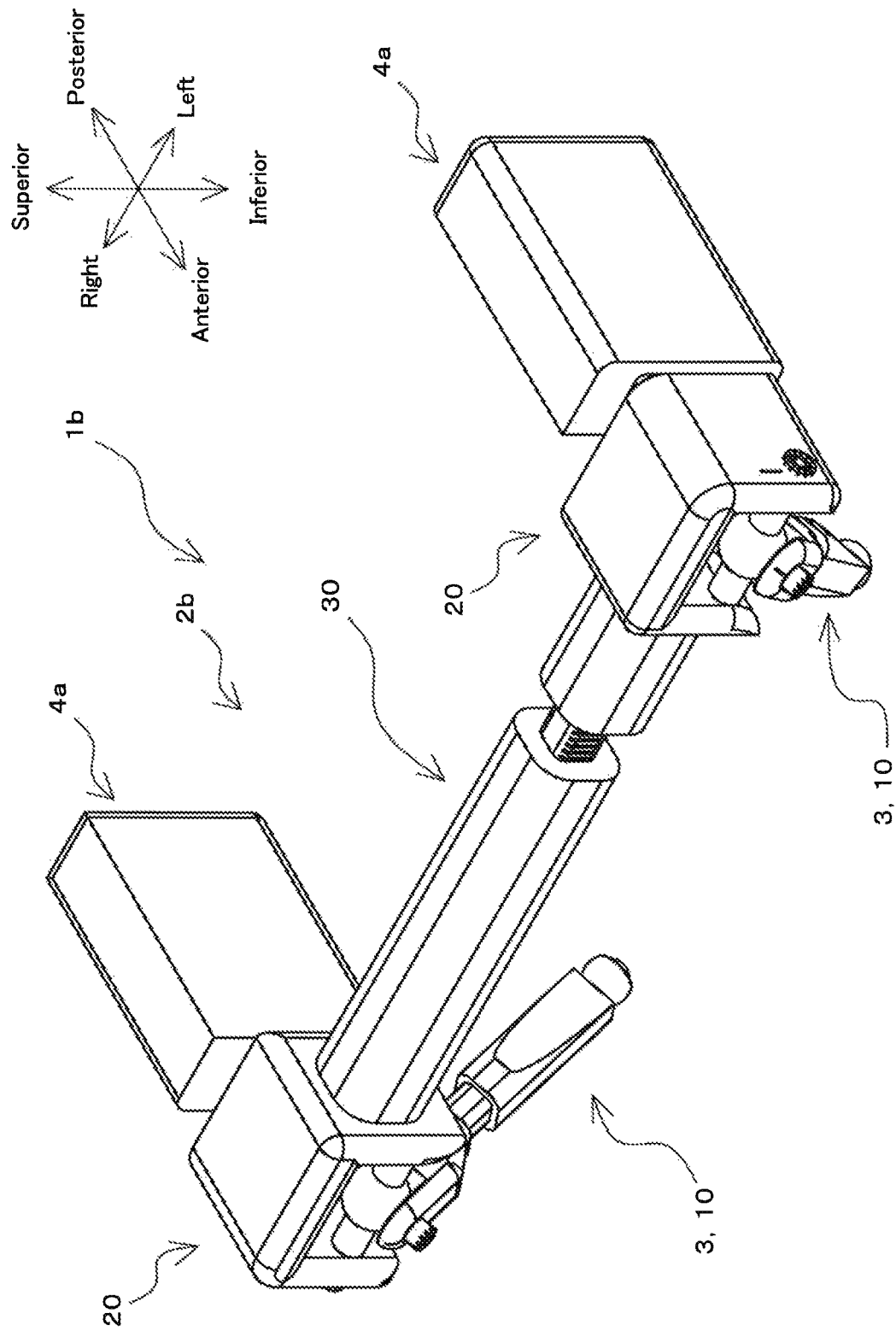
FIG. 10 is a perspective view of a femoral head position determining instrument according to a modified example.

(2) FIG. 10 is a perspective view of a femoral head position determining instrument 1*b* according to a modified example. The femoral head position determining instrument 1 according to the above-described embodiment has a configuration in which the contact plates 6 can be attached to and detached from the contact plate attachment portions 5, but there is no limitation thereto. Specifically, as shown in FIG. 10, a holding portion 4*a* may be configured by one plate-shaped member. Accordingly, the work of manufacturing parts (contact plates 6 in the case of the femoral head position determining instrument 1 shown in FIG. 1) depending on the patient P can be omitted, and an instrument including a holding mechanism 2*b* that can be used for any patient P can be provided. It should be noted that, in this case, a portion of one holding portion 4*a* that faces the other holding portion 4*a* functions as a contact portion with which the anterior superior iliac spine of the patient is to be brought into contact.

Figure 11:
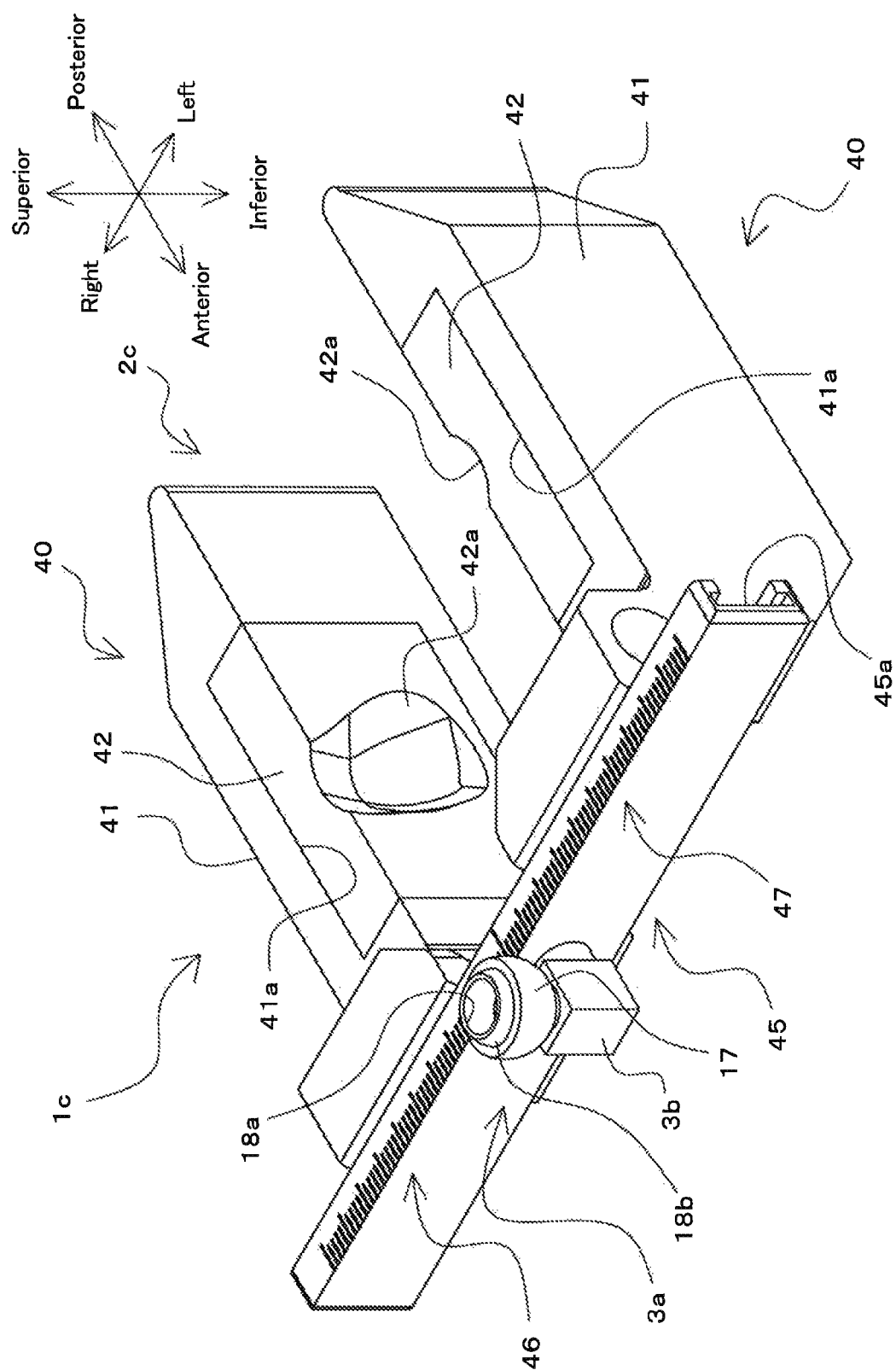
FIG. 11 is a perspective view of a second metatarsal bone position determining instrument according to an embodiment.
Figure 12:
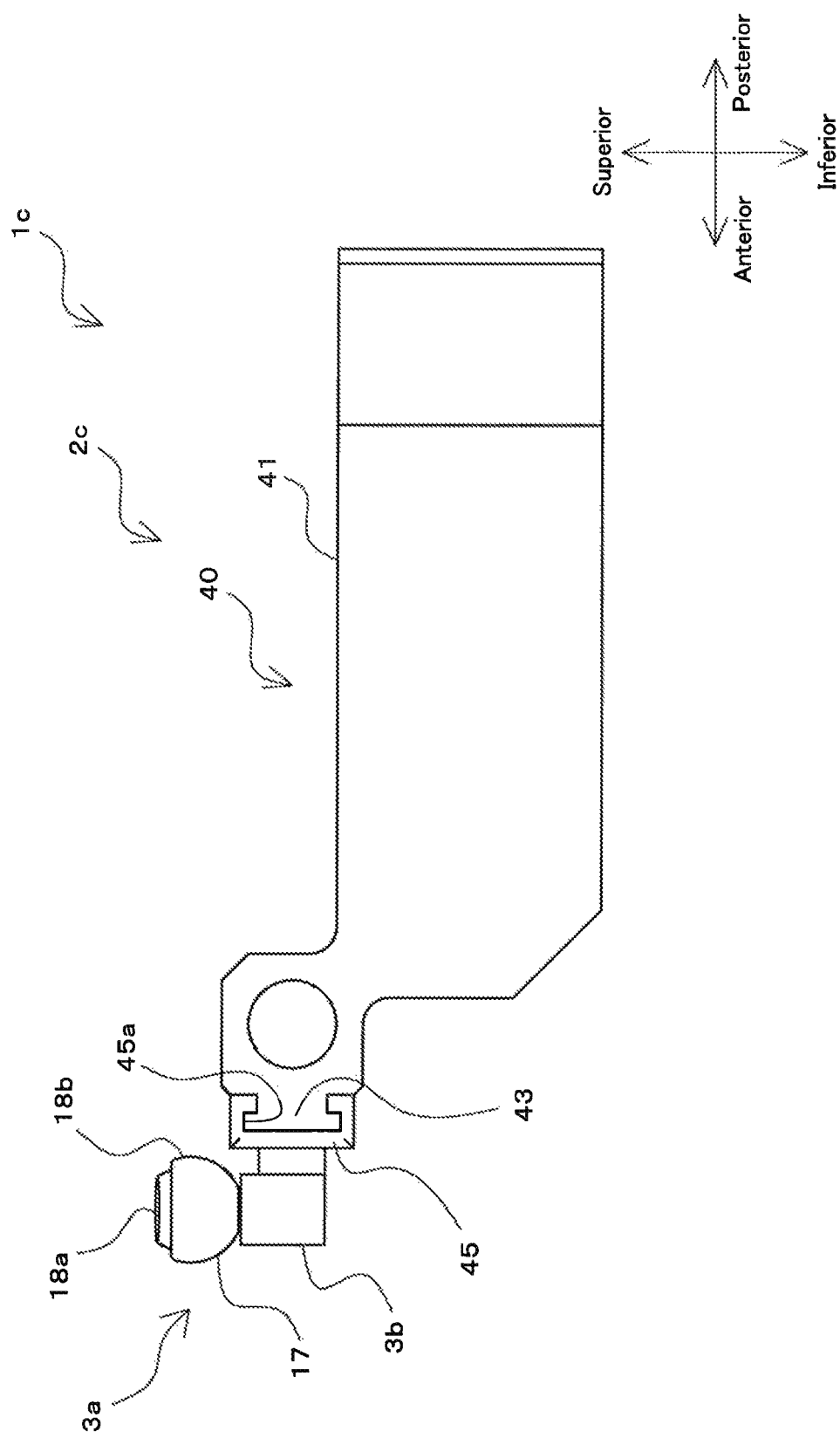
FIG. 12 is a side view of the second metatarsal bone position determining instrument shown in FIG. 11.

(3) FIG. 11 is a perspective view of a second metatarsal bone position determining instrument 1*c* according to an embodiment. FIG. 12 is a side view of the second metatarsal bone position determining instrument 1*c* shown in FIG. 11. In the embodiment and the modified examples described above, the femoral head position determining instruments 1, 1*a*, and 1*b* for finding the positions of the femoral heads 56 have been described as examples of an instrument for artificial knee joint replacement surgery, but the second metatarsal bone position determining instrument 1*c* shown in FIGS. 11 and 12 can be taken as another example of the instrument for artificial knee joint replacement surgery. The second metatarsal bone position determining instrument 1*c* is used in order that an operator finds the position of the second metatarsal bone of a patient.

Overall Configuration

As shown in FIGS. 11 and 12, the second metatarsal bone position determining instrument 1*c* includes a holding mechanism 2*c* and an indicating mechanism 3*a*.

The holding mechanism 2*c* includes a pair of holding portions 40 and a connecting portion 45.

The two holding portions 40 have the same shape. Each of the holding portions 40 includes a contact plate attachment portion 41 (contact portion attachment portion) and a contact plate 42 (contact portion) in the same manner as in the above-described embodiment.

In the same manner as the contact plate attachment portion 5 of the femoral head position determining instrument 1 shown in FIG. 1, the contact plate attachment portion 41 is a portion that is formed in a substantially plate shape having a predetermined thickness in the horizontal direction, and an accommodating recessed portion 41*a* in which the contact plate 42 is accommodated is formed in a portion on the inner side of the contact plate attachment portion 41.

A projection 43 that is to be fitted to a groove portion 45*a* formed in the connecting portion 45, which will be described in detail later, and that can be slid and moved along the groove portion 45*a* in the horizontal direction is formed in the contact plate attachment portion 41. This projection 43 is formed to extend in the horizontal direction.

In the same manner as the contact plate 6 of the femoral head position determining instrument 1 shown in FIG. 1, the contact plate 42 is formed to have a size that allows the contact plate 42 to be attached to and detached from the accommodating recessed portion 41*a* of the contact plate attachment portion 41, and thus can be attached to and detached from the accommodating recessed portion 41*a*. A recessed portion 42*a* for a malleolus (recessed portion for a contact target) into which the malleolus of a patient is fitted in a state in which the second metatarsal bone position determining instrument 1*c* is fixed to an ankle of the patient is formed in the contact plate 42. The contact plate 42 is accommodated in the contact plate attachment portion 41 and fixed such that the recessed portion 42*a* for a malleolus faces inward.

The contact plate 42 is tailored to a patient on whom surgery is to be performed. Specifically, the contact plate 42 is formed in a shape that allows the recessed portion 42a for a malleolus to be fitted to the malleolus of the patient (the medial malleolus at the distal end of the fibula of the patient or the lateral malleolus at the distal end of the tibia of the patient) in a state in which the second metatarsal bone position determining instrument 1c is attached to an ankle of the patient. More specifically, the recessed portion 42a for a malleolus of the right contact plate 42 is formed in a shape that is fitted to one of the medial malleolus and the lateral malleolus, whereas the recessed portion 42a for a malleolus of the left contact plate 42 is formed in a shape that is fitted to the other of the medial malleolus and the lateral malleolus. Accordingly, the second metatarsal bone position determining instrument 1c can be fitted to the patient.

Furthermore, the contact plate 42 is manufactured as described below based on the shapes of the bones at the ankle of the patient. Specifically, the contact plate 42 is formed such that the position of the second metatarsal bone of a patient held between the contact plates 42 corresponds to the position of the indicating mechanism 3a, which will be described in detail later, in the horizontal direction.

The connecting portion 45 is a member formed in an elongated shape extending in the horizontal direction, and the groove portion 45a into which the projection 43 of the contact plate 42 is to be fitted is formed in the connecting portion 45 to extend in the longitudinal direction of the connecting portion 45. The indicating mechanism 3a is fixed to the central portion of the connecting portion 45 in the longitudinal direction (horizontal direction). Furthermore, the portion to which the indicating mechanism 3a is fixed is taken as a reference position, and a right indicator 46 for measuring the distance between the reference position and the right holding portion 40 and a left indicator 47 for measuring the distance between the reference position and the left holding portion 40 are formed in the connecting portion 45.

The indicating mechanism 3a is fixed to the central portion of the connecting portion 45 in the horizontal direction. The indicating mechanism 3a includes a projecting portion 3b that projects forward from the front surface of the connecting portion 45, a bowl-shaped portion 17 that is provided on the top portion of the front end portion of the projecting portion 3b, and a ball-shaped member that is accommodated in the bowl-shaped portion 17. This ball-shaped member is provided as a second metatarsal bone position indicating portion 18b (position identification target indicating portion) for indicating the position of the second metatarsal bone of the patient in a state in which the second metatarsal bone position determining instrument 1c is attached to the patient. In the same manner as in the above-mentioned embodiment, an attachment hole portion 18a to which the front end portion of the alignment rod 60 is attached is formed in the second metatarsal bone position indicating portion 18b. It should be noted that the shape of the bowl-shaped portion 17 in the second metatarsal bone position determining instrument 1c is similar to the shape of the bowl-shaped portion 17 in the above-described femoral head position determining instrument 1, and the shape of the second metatarsal bone position indicating portion 18b is similar to the shape of the head position indicating portion 18 in the above-described femoral head position determining instrument 1, and therefore, detailed description thereof is omitted.

Usage Method

In order to use the second metatarsal bone position determining instrument 1c according to this embodiment, first, in the same manner as in the above-described femoral head position determining instrument 1, the contact plates 42 are tailored to a patient on whom surgery is to be performed. Specifically, first, the shapes of the bones at the ankle of the patient are modeled using X-rays or the like, and each of the pair of contact plates 42 is formed based on this model. At this time, the contact plates 42 are formed such that the position of the indicating mechanism 3a in the horizontal direction corresponds to the position of the second metatarsal bone of the patient in a state in which the medial malleolus or the lateral malleolus of the patient is fitted into the recessed portion 42a for a malleolus formed in each of the contact plates 42. The contact plates 42 formed in this manner are respectively accommodated in the accommodating recessed portions 41a of the corresponding contact plate attachment portions 41 and fixed.

Next an operator fixes the second metatarsal bone position determining instrument 1c equipped with the contact plates 42 formed as described above to the patient. Specifically, the operator slides the position of one of the holding portion 40 relative to the connecting portion 45 based on a distance between the second metatarsal bone and the medial malleolus or lateral malleolus in the horizontal direction of the patient that has been calculated based on the modeled shape of the bones near the ankle of the patient, while checking the right indicator 46 (or the left indicator 47). In a state in which a malleolus of the patient is fitted into the recessed portion 42a for a malleolus of the one holding portion 40 slid based on the aforementioned distance, the other holding portion 40 is slid inward to hold the malleoli of the patient therebetween from both sides. Accordingly, the second metatarsal bone position determining instrument 1c can be fixed to the ankle of the patient, and the second metatarsal bone position indicating portion 18b can be accurately arranged at the position of the second metatarsal bone of the patient.

Next, the operator attaches the front end portion of the alignment rod 60 to the attachment hole portion 18a of the second metatarsal bone position indicating portion 18b arranged at a position of the second metatarsal bone as described above. Accordingly, the operator can confirm alignment while changing the orientation of the alignment rod 60 about the second metatarsal bone position indicating portion 18b as the center.

The operator can determine the position of cross sections of the knee joint (specifically, the distal end of the femur and the proximal end of the tibia) while confirming the alignment as described above, and therefore, the cross sections on which an artificial knee joint is provided can be formed appropriately.

Effects

As described above, with the second metatarsal bone position determining instrument 1c according to this embodiment, the second metatarsal bone position indicating portion 18b is arranged at a position corresponding to the second metatarsal bone in a state in which the contact plates 42 are in contact with the medial malleolus and the lateral malleolus of a patient. At this time, the second metatarsal bone position indicating portion 18b is arranged based on the relative positional relationship between the medial malleolus or lateral malleolus and the second metatarsal bone of the patient. Accordingly, the second metatarsal bone position indicating portion 18b can be accurately arranged at a position corresponding to the second metatarsal bone. The operator who is to perform artificial knee joint replacement surgery can directly and visually observe the second metatarsal bone position indicating portion 18b arranged as described above and thus easily find the position of the second metatarsal bone of the patient.

Therefore, with the second metatarsal bone position determining instrument 1c, the position of the second metatarsal bone of the patient can be easily identified. In addition, the position of the second metatarsal bone position indicating portion 18b determined as described above accurately corresponds to the position of the second metatarsal bone, and thus alignment can be obtained with high accuracy.

Also, with the second metatarsal bone position determining instrument 1c, the second metatarsal bone position indicating portion 18b is arranged at a position corresponding to the position of the second metatarsal bone based on the positional relationship between the lateral malleolus (or the medial malleolus) and the second metatarsal bone that was obtained in advance prior to the surgery in a state in which the contact plates 42 are in contact with the lateral malleolus at the distal end of the fibula or the medial malleolus at the distal end of the tibia. The lateral malleolus and the medial malleolus are portions (so-called malleoli) that protrude laterally at the distal end of the lower limb and are covered with only a very thin layer (e.g., skin). That is, the relative positional relationship between the contact plate 42 brought into contact with the lateral malleolus (or the medial malleolus) via this thin layer and the second metatarsal bone position indicating portion 18b is substantially the same as the previously obtained relative positional relationship between the lateral malleolus (or the medial malleolus) and the second metatarsal bone. Accordingly, a large positional difference between the position of the second metatarsal bone position indicating portion 18b and the actual position of the second metatarsal bone can be prevented. Therefore, with this configuration, the position of the second metatarsal bone can be accurately understood.

Also, with the second metatarsal bone position determining instrument 1c, the lateral malleolus at the distal end of the fibula and the medial malleolus at the distal end of the tibia are held between the pair of contact plates 42, and thus the second metatarsal bone position determining instrument 1c can be easily fixed to the patient.

Also, with the second metatarsal bone position determining instrument 1c, the position of the contact plate 42 relative to a reference position (position at which the second metatarsal bone position indicating portion 18b is provided) of the connecting portion 45 is adjusted based on the positional relationship between the lateral malleolus at the distal end of the fibula (or the medial malleolus at the distal end of the tibia) and the second metatarsal bone of the patient that was obtained in advance through modeling of the bones of the patient, or the like. Specifically, the operator can match the distance between the reference position and the contact plate 42 with the distance between the second metatarsal bone and the lateral malleolus (or medial malleolus) of the patient obtained through modeling or the like while checking the right indicator 46 or the left indicator 47. Accordingly, the second metatarsal bone position indicating portion 18b can be accurately arranged at the position of the second metatarsal bone.

Figure 13:
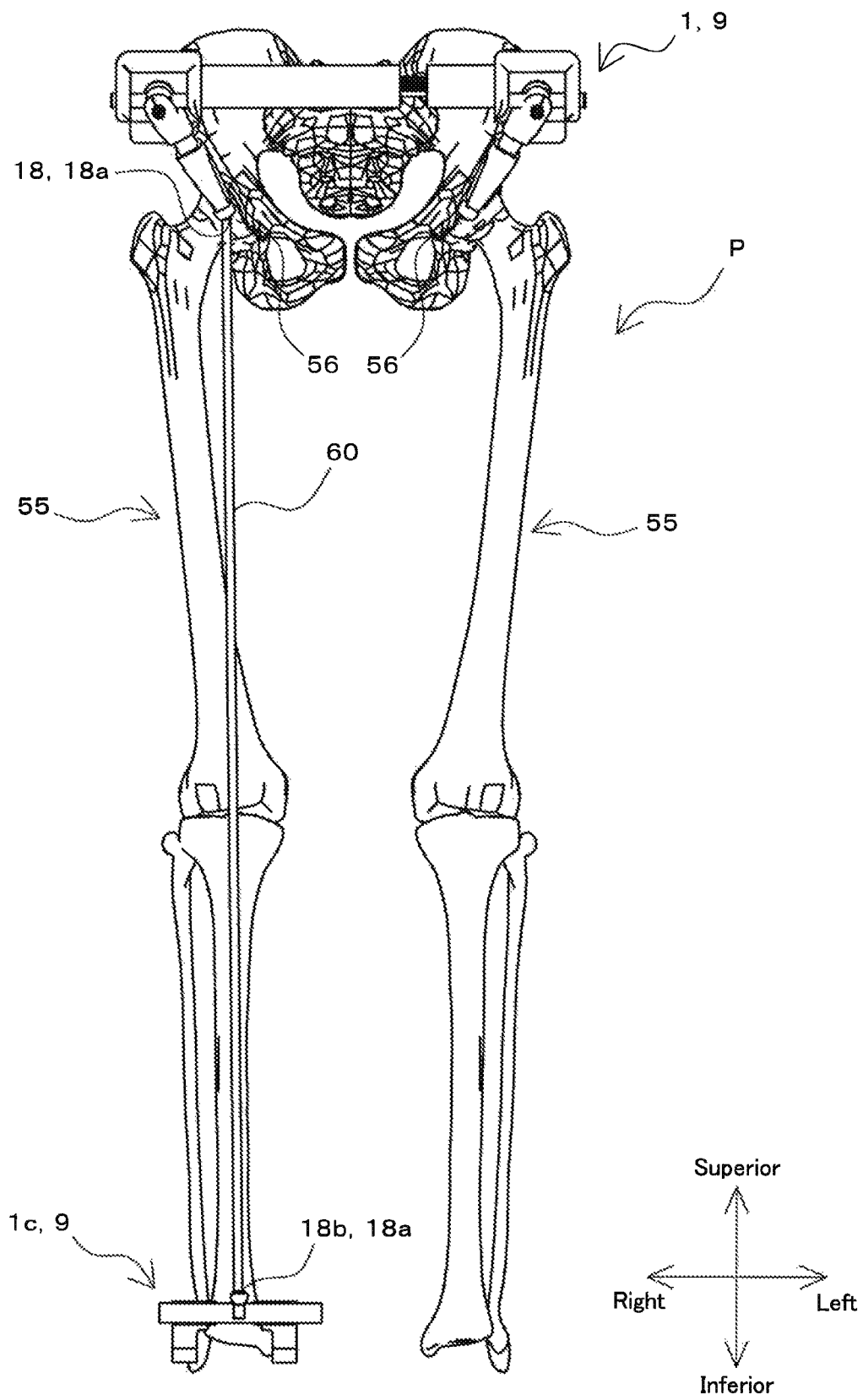
FIG. 13 is a diagram illustrating a state in which an instrument unit for artificial knee joint replacement surgery according to an embodiment is fixed to a patient.

FIG. 13 is a diagram illustrating a state in which an instrument unit 9 for artificial knee joint replacement surgery according to an embodiment of the present invention is fixed to a patient. The instrument unit 9 for artificial knee joint replacement surgery includes the above-described femoral head position determining instrument 1 and the second metatarsal bone position determining instrument 1c.

With the instrument unit 9 for artificial knee joint replacement surgery, it can be easily confirmed whether or not the center of the femoral head 56, the knee joint center, and the second metatarsal bone of the patient P are aligned in a straight line during and after the surgery, for example. Specifically, the instrument unit 9 for artificial knee joint replacement surgery is used in a state in which both the femoral head position determining instrument 1 and the second metatarsal bone position determining instrument 1c are fixed to the patient P on whom the surgery has been performed. The operator attaches one end portion of the alignment rod 60 to the attachment hole portion 18a of the head position indicating portion 18 of the femoral head position determining instrument 1, and attaches the other end portion of the alignment rod 60 to the attachment hole portion 18a of the second metatarsal bone position indicating portion 18b of the second metatarsal bone position determining instrument 1c. At this time, when the knee joint center overlaps the alignment rod 60 as shown in FIG. 13, it can be confirmed that the femoral head center, the knee joint center, and the second metatarsal bone center are aligned in a straight line, that is, are in alignment. On the other hand, when there is a positional difference between the alignment rod 60 and the knee joint center, it can be confirmed that they do not align with one another, thus making it possible to determine whether or not osteotomy needs to be performed again based on the amount of the positional difference.

The present invention is broadly applicable as an instrument for finding the position of a predetermined portion (particularly a femoral head or a second metatarsal bone) in a patient on whom artificial knee joint replacement surgery is to be performed.

The invention claimed is:

1. An instrument for artificial knee joint replacement surgery, comprising:
a holding mechanism that includes a holding portion having a contact portion to be brought into contact with one of a left anterior superior iliac spine and a right anterior superior iliac spine of a patient on whom artificial knee joint replacement surgery is to be performed and that holds the patient in a state in which the contact portion is in contact with one of the left anterior superior iliac spine and the right anterior superior iliac spine; and
an indicating mechanism that includes a femoral head indicating portion to be arranged at a position corresponding to a femoral head in a state in which the holding mechanism holds the patient, the femoral head being a portion whose position is to be identified in the patient, and that is configured to attach to the holding mechanism,
wherein a position at which the femoral head indicating portion is to be arranged is determined based on a positional relationship between one of the left anterior superior iliac spine and the right anterior superior iliac spine and the femoral head that is obtained in advance prior to surgery,
wherein a hole portion into which an end portion of an alignment rod is to be inserted is formed in the femoral head indicating portion,
wherein the indicating mechanism includes a base end portion that is a portion located on a base end side, and a front end portion that is a portion located on a front end side,
the base end portion is attached to the holding mechanism, the front end portion is formed to extend in a direction away from the base end portion, and the femoral head indicating portion is provided at a front end of the front end portion, and wherein the front end portion can be moved relative to the base end portion in a direction in which the front end portion extends.

2. The instrument for artificial knee joint replacement surgery according to claim 1, wherein a recessed portion for one of the left anterior superior iliac spine and the right anterior superior iliac spine into which one of the left anterior superior iliac spine and the right anterior superior iliac is to be fitted is formed in the contact portion.

3. The instrument for artificial knee joint replacement surgery according to claim 2, wherein the holding portion further includes a contact portion attachment portion with the contact portion being attachable thereto and detachable therefrom, and one of the left anterior superior iliac spine and the right anterior superior iliac spine is to be fitted into the recessed portion for one of the left anterior superior iliac spine and the right anterior superior iliac spine of the contact portion attached to the contact portion attachment portion.

4. The instrument for artificial knee joint replacement surgery according to claim 2, wherein the recessed portion for one of the left anterior superior iliac spine and the right anterior superior iliac spine is formed based on a shape of one of the left anterior superior iliac spine and the right anterior superior iliac spine in the patient.

5. The instrument for artificial knee joint replacement surgery according to 1, wherein the holding mechanism further includes:
a pair of the holding portions; and
a connecting portion that connects the pair of the holding portions, and the holding mechanism holds the patient by the contact portions of the pair of the holding portions holding a pair of one of the left anterior superior iliac spine and the right anterior superior iliac spine therebetween.

6. The instrument for artificial knee joint replacement surgery according to claim 1, wherein the holding mechanism further includes a universal joint portion, and the base end portion is attached to the universal joint portion.

7. The instrument for artificial knee joint replacement surgery according to claim 1, wherein the holding mechanism further includes:
a pair of the contact portions; and
a connecting portion that connects the pair of the contact portions, and one of the pair of the contact portions is configured to be brought into contact with the lateral malleolus at the distal end of the fibula, an other one of the pair of the contact portions is configured to be brought into contact with the medial malleolus at the distal end of the tibia, and the contact portions can be moved along the connecting portion.

8. The instrument for artificial knee joint replacement surgery according to claim 7, wherein the femoral head indicating portion is provided in the connecting portion, and
an indicator for measuring a distance between a reference position of the connecting portion that corresponds to a position at which the femoral head indicating portion is provided and the contact portion is formed in the connecting portion.

9. An instrument unit for artificial knee joint replacement surgery, comprising:
the instrument according to claim 1 serving as a femoral head position determining instrument; and
the instrument according to claim 1 serving as a second metatarsal bone position determining instrument.

10. An instrument for artificial knee joint replacement surgery, comprising:
a holding mechanism that includes a holding portion having a contact portion to be brought into contact with one of a left anterior superior iliac spine and a right anterior superior iliac spine of a patient on whom artificial knee joint replacement surgery is to be performed and that holds the patient in a state in which the contact portion is in contact with one of the left anterior superior iliac spine and the right anterior superior iliac spine; and
an indicating mechanism that includes a femoral head indicating portion to be arranged at a position corresponding to a femoral head in a state in which the holding mechanism holds the patient, the femoral head being a portion whose position is to be identified in the patient, and that is attached to the holding mechanism,
wherein a position at which the femoral head indicating portion is to be arranged is determined based on a positional relationship between one of the left anterior superior iliac spine and the right anterior superior iliac spine and the femoral head that is obtained in advance prior to surgery,
wherein a recessed portion for one of the left anterior superior iliac spine and the right anterior superior iliac spine into which one of the left anterior superior iliac spine and the right anterior superior iliac spine is to be fitted is formed in the contact portion,
wherein the recessed portion for one of the left anterior superior iliac spine and the right anterior superior iliac spine is formed based on a shape of one of the left anterior superior iliac spine and the right anterior superior iliac spine in the patient,
wherein the indicating mechanism includes a base end portion that is a portion located on a base end side, and a front end portion that is a portion located on a front end side,
the base end portion is attached to the holding mechanism,
the front end portion is formed to extend in a direction away from the base end portion, and the femoral head indicating portion is provided at a front end of the front end portion, and
wherein the front end portion can be moved relative to the base end portion in a direction in which the front end portion extends.

* * * * *